(12) United States Patent
Nishimura et al.

(10) Patent No.: US 12,264,212 B2
(45) Date of Patent: Apr. 1, 2025

(54) COPOLYMER FOR SUPPRESSING PROTEIN ADSORPTION, METHOD FOR PRODUCING COPOLYMER, RESIN MODIFIER, MOLDING MATERIAL, COPOLYMER-CONTAINING COMPOSITION, COATING FILM, AND ARTICLE

(71) Applicant: Mitsubishi Chemical Corporation, Tokyo (JP)

(72) Inventors: Masanari Nishimura, Tokyo (JP); Kazunori Mukunoki, Tokyo (JP); Taeko Oonuma, Tokyo (JP); Hiromi Aso, Tokyo (JP); Yumiko Saeki, Tokyo (JP)

(73) Assignee: Mitsubishi Chemical Corporation, Tokyo (JP)

( * ) Notice: Subject to any disclaimer, the term of this patent is extended or adjusted under 35 U.S.C. 154(b) by 1007 days.

(21) Appl. No.: 17/205,281

(22) Filed: Mar. 18, 2021

(65) Prior Publication Data

US 2021/0206896 A1 Jul. 8, 2021

Related U.S. Application Data

(63) Continuation of application No. PCT/JP2019/036040, filed on Sep. 13, 2019.

(30) Foreign Application Priority Data

Sep. 26, 2018 (JP) .................................. 2018-180898
Mar. 14, 2019 (JP) .................................. 2019-047265

(51) Int. Cl.
*C08F 220/06* (2006.01)
*C08F 2/18* (2006.01)
(Continued)

(52) U.S. Cl.
CPC .............. *C08F 220/06* (2013.01); *C08F 2/18* (2013.01); *C08F 212/08* (2013.01);
(Continued)

(58) Field of Classification Search
None
See application file for complete search history.

(56) References Cited

U.S. PATENT DOCUMENTS 5,684,913 A 11/1997 Sugiyama et al.
2002/0064558 A1 5/2002 Tanaka et al.
(Continued)

FOREIGN PATENT DOCUMENTS

CN 108137760 A 6/2018
GB 2 152 947 A 8/1985
(Continued)

OTHER PUBLICATIONS

Japanese Office Action issued May 9, 2023 in Japanese Patent Application No. 2020-548456 (with unedited computer-generated English Translation), 10 pages.
(Continued)

*Primary Examiner* — Robert S Jones, Jr.
*Assistant Examiner* — Jiangtian Xu
(74) *Attorney, Agent, or Firm* — Oblon, McClelland, Maier & Neustadt, L.L.P.

(57) ABSTRACT

There is provided a copolymer for suppressing protein adsorption, which contains a constitutional unit (a) represented by Formula 1 and a constitutional unit (b) represented by Formula 2, and which is used for producing an article that comes in contact with a protein. In the formula, $R^1$ represents a hydrogen atom or a methyl group, $R^2$ represents an $OR^{33}$, a halogen atom, $COR^{34}$, $COOR^{35}$, CN, $CONR^{36}R^{37}$, or $R^{38}$, where $R^{33}$ to $R^{37}$ each independently represent a
(Continued)

hydrogen atom, a substituted or unsubstituted alkyl group, a substituted or unsubstituted alicyclic group, a substituted or unsubstituted aryl group, a substituted or unsubstituted heteroaryl group, a substituted or unsubstituted non-aromatic heterocyclic group, a substituted or unsubstituted aralkyl group, a substituted or unsubstituted alkaryl group, or a substituted or unsubstituted organosilyl group, and $R^{38}$ represents a substituted or unsubstituted aryl group or a substituted or unsubstituted heteroaryl group.

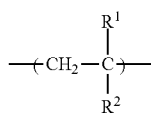

(1)

15 Claims, 1 Drawing Sheet

(51) Int. Cl.
   *C08F 212/08* (2006.01)
   *C08K 5/00* (2006.01)
   *C09D 125/06* (2006.01)
   *C09D 133/10* (2006.01)

(52) U.S. Cl.
   CPC .......... *C08K 5/0025* (2013.01); *C09D 125/06* (2013.01); *C09D 133/10* (2013.01)

(56) References Cited

U.S. PATENT DOCUMENTS

| | | |
|---|---|---|
| 2012/0024779 A1 | 2/2012 | Ochiai et al. |
| 2014/0194557 A1 | 7/2014 | Hayashi et al. |
| 2015/0343392 A1 | 12/2015 | Hikita et al. |
| 2016/0185893 A1 | 6/2016 | Oonuma et al. |
| 2016/0237192 A1 | 8/2016 | Fujiyama et al. |
| 2017/0087520 A1 | 3/2017 | Hikita et al. |
| 2018/0147776 A1* | 5/2018 | Kotani .................. B33Y 70/00 |
| 2018/0201797 A1 | 7/2018 | Taniguchi et al. |
| 2019/0077898 A1 | 3/2019 | Otani et al. |
| 2020/0023322 A1 | 1/2020 | Hikita et al. |
| 2020/0164112 A1 | 5/2020 | Kato et al. |

FOREIGN PATENT DOCUMENTS

| | | | |
|---|---|---|---|
| JP | 60-086105 | | 5/1985 |
| JP | 60-158211 | A | 8/1985 |
| JP | 4-152962 | A | 6/1992 |
| JP | 4-194816 | A | 7/1992 |
| JP | 4-361037 | | 12/1992 |
| JP | 8-184715 | A | 7/1996 |
| JP | 2001-106742 | A | 4/2001 |
| JP | 2002-105136 | A | 4/2002 |
| JP | 2004-161954 | A | 6/2004 |
| JP | 2006291073 | A * | 10/2006 |
| JP | 2013-023540 | | 2/2013 |
| JP | 2013-057058 | A | 3/2013 |
| JP | 2013-121430 | A | 6/2013 |
| JP | 2018-9137 | | 1/2018 |
| JP | 2019-99727 | A | 6/2019 |
| WO | WO 2014/098234 | A1 | 6/2014 |
| WO | WO 2017/051922 | A1 | 3/2017 |
| WO | WO 2017/099113 | A1 | 6/2017 |
| WO | WO 2017/199562 | A1 | 11/2017 |
| WO | WO 2018/181365 | A1 | 10/2018 |
| WO | WO 2018/207586 | A1 | 11/2018 |

OTHER PUBLICATIONS

Combined Chinese Office Action and Search Report issued Dec. 28, 2022, in corresponding Chinese Patent Application No. 201980062062.6 (with English Translation), 14 pages.
Extended European Search Report issued Oct. 26, 2021 in corresponding European Patent Application No. 19866852.7, 7 pages.
Indian Office Action issued Oct. 21, 2022 in Indian Patent Application No. 202117016064, 6 pages.
Office Action issued Dec. 12, 2023, in corresponding European Patent Application No. 19866852.7, 5 pages.
European Office Action issued Jun. 27, 2023 in European Patent Application No. 19866852.7, 4 pages.
Office Action issued Sep. 22, 2023. in corresponding Chinese Patent Application No. 201980062062.6 (with English Translation), 14 pages.
International Search Report issued Dec. 3, 2019 in PCT/JP2019/036040 filed Sep. 13, 2019 (with English translation), 4 pages.
Decision of Rejection issued Jan. 17, 2024, in corresponding Chinese Patent Application No. 201980062062.6 (with English Translation), 14 pages.
Hearing Notice issued Jan. 31, 2024, in corresponding Indian Patent Application No. 202117016064 (with English Translation), 3 pages.
Japanese Notice of Reasons for Refusal issued Jul. 9, 2024 in Japanese Application No. 2023-110980 with English Machine translation, 13 pgs.
Office Action mailed Nov. 19, 2024, in corresponding Japanese Patent Application No. 2023-110980 (with machine translation).

* cited by examiner

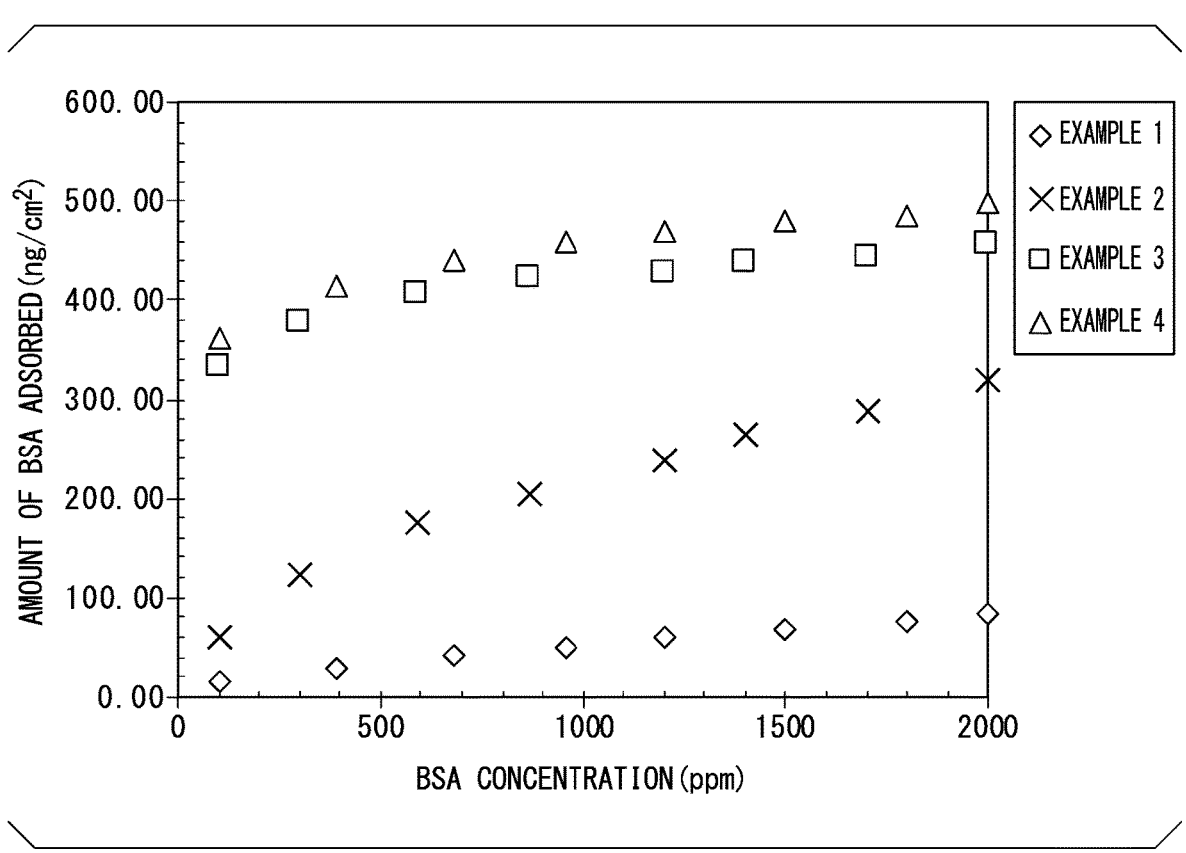

COPOLYMER FOR SUPPRESSING PROTEIN ADSORPTION, METHOD FOR PRODUCING COPOLYMER, RESIN MODIFIER, MOLDING MATERIAL, COPOLYMER-CONTAINING COMPOSITION, COATING FILM, AND ARTICLE

This application is a continuation application of International Application No. PCT/JP2019/036040, filed on Sep. 13, 2019, which claims the benefit of priority of the prior Japanese Patent Application No. 2018-180898, filed Sep. 26, 2018, and the prior Japanese Patent Application No. 2019-047265 filed Mar. 14, 2019, the contents of which are incorporated herein by reference.

TECHNICAL FIELD

The present invention relates to a copolymer for suppressing protein adsorption, a method for producing copolymer, and a resin modifier, a molding material, a copolymer-containing composition, a coating film, and an article, which are obtained by using the copolymer.

BACKGROUND ART

In recent years, in the fields of medical instruments, biochemical analysis, and protein separation and purification, various polymer materials (polystyrene, polypropylene, polyethylene, polyurethane, polyvinyl chloride, and nylon), glass, or metals such as stainless steel have been used for various component parts for various reaction vessels, centrifuge tubes, tubes, syringes, pipettes, filters, separation columns, and the like, containers, and the like. However, protein adsorption occurs in any materials described above, which is a cause of the low reproducibility of detection sensitivity or poor purification.

In addition, artificial organs such as a catheter, a cannula, a stent, a plasma separation membrane, and an artificial heart and lung come in contact with circulating blood, a metabolite in the body, and the like. As a result, there is a need for biocompatibility that suppresses the formation of a thrombus or the like, which is caused by the protein adsorption or the plasma protein adsorption.

Patent Document 1 describes that polymethoxyethyl acrylate (PMEA) has biocompatibility such as antithrombotic property and low protein adsorption ability.

Patent Document 2 discloses a method for obtaining a film to which a platelet is difficult to adsorb by heat-treating a coating film obtained from a blending solution of polymethyl methacrylate (PMMA) and PMEA and exposing the coating film to ultrapure water.

CITATION LIST

Patent Document

[Patent Document 1]
Japanese Unexamined Patent Application, First Publication No. 2004-161954
[Patent Document 2]
Japanese Unexamined Patent Application, First Publication No. 2013-121430

SUMMARY OF INVENTION

Technical Problem

However, the PMEA disclosed in Patent Document 1 has a very low glass transition temperature of about −50° C. Therefore, it is difficult to use the PMEA as a molding material, and in a case where it is used as a coating material, a coating film obtained therefrom is difficult to have sufficient hardness, thereby being inferior in practicality.

Further, the method disclosed in Patent Document 2 has a drawback in that the producing process is complicated and the processing time is long.

The present invention provides a copolymer for suppressing protein adsorption to which a protein is difficult to adsorb and which is suitable for producing an article that comes in contact with a protein, a method for producing copolymer, and a resin modifier, a molding material, a copolymer-containing composition, a coating film, and an article, which are obtained by using the copolymer.

Solution to Problem

The present invention has the following aspects.

[1] A copolymer for suppressing protein adsorption, containing a constitutional unit (a) represented by Formula (1) and a constitutional unit (b) represented by Formula (2).

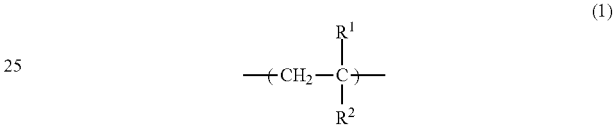

(In the formula, $R^1$ represents a hydrogen atom or a methyl group, $R^2$ is an $OR^{33}$, a halogen atom, $COR^{34}$, $COOR^{35}$, CN, $CONR^{36}R^{37}$, or $R^{38}$, where $R^{33}$ to $R^{37}$ each independently represent a hydrogen atom, a substituted or unsubstituted alkyl group, a substituted or unsubstituted alicyclic group, a substituted or unsubstituted aryl group, a substituted or unsubstituted heteroaryl group, a substituted or unsubstituted non-aromatic heterocyclic group, a substituted or unsubstituted aralkyl group, a substituted or unsubstituted alkaryl group, or a substituted or unsubstituted organosilyl group, and $R^{38}$ represents a substituted or unsubstituted aryl group or a substituted or unsubstituted heteroaryl group.)

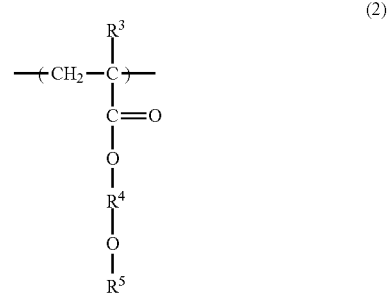

(In the formula, $R^3$ represents a hydrogen atom or a methyl group, $R^4$ represents an alkylene group having 1 to 4 carbon atoms, and $R^5$ represents a hydrocarbon group having 1 to 6 carbon atoms.)

[2] The copolymer for suppressing protein adsorption according to [1], in which the constitutional unit (a) is a constitutional unit derived from a (meth)acrylic acid ester.

[3] The copolymer for suppressing protein adsorption according to [1] or [2], further containing a constitutional unit (d) derived from a macromonomer containing the constitutional unit (a).

[4] The copolymer for suppressing protein adsorption according to [3], in which the macromonomer is represented by Formula (4).

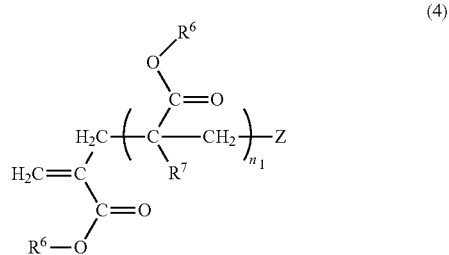

(In the formula, $R^6$'s each independently represent a hydrogen atom, an alkyl group which is unsubstituted or has a substituent, an alicyclic group which is unsubstituted or has a substituent, an aryl group which is unsubstituted or has a substituent, a heteroaryl group which is unsubstituted or has a substituent, or a non-aromatic heterocyclic group which is unsubstituted or has a substituent, where a plurality of $R^6$'s may be the same or different from each other, les represent a hydrogen atom or a methyl group, where a plurality of $R^7$'s may be the same or different from each other, Z is a terminal group, and m is a natural number of 2 to 10,000.)

[5] The copolymer for suppressing protein adsorption according to any one of [1] to [4], in which the constitutional unit (b) is derived from a monomer selected from the group consisting of methoxymethyl acrylate, methoxyethyl acrylate, methoxypropyl acrylate, methoxybutyl acrylate, ethoxymethyl acrylate, ethoxyethyl acrylate, ethoxypropyl acrylate, ethoxybutyl acrylate, propoxymethyl acrylate, propoxyethyl acrylate, propoxypropyl acrylate, propoxybutyl acrylate, butoxymethyl acrylate, butoxyethyl acrylate, butoxypropyl acrylate, butoxybutyl acrylate, methoxymethyl methacrylate, methoxyethyl methacrylate, methoxypropyl methacrylate, methoxybutyl methacrylate, ethoxymethyl methacrylate, ethoxyethyl methacrylate, ethoxypropyl methacrylate, ethoxybutyl methacrylate, propoxymethyl methacrylate, propoxyethyl methacrylate, propoxypropyl methacrylate, propoxybutyl methacrylate, butoxymethyl methacrylate, butoxyethyl methacrylate, butoxypropyl methacrylate, and butoxybutyl methacrylate.

[6] The copolymer for suppressing protein adsorption according to any one of [1] to [5], in which the copolymer has a weight-average molecular weight (Mw) of 75,000 or more.

[7] The copolymer for suppressing protein adsorption according to any one of [1] to [6], in which a total mass of the constitutional unit (b) is more than a total mass of the constitutional unit (a) in all constitutional units.

[8] A resin modifier made of the copolymer for suppressing protein adsorption according to any one of [1] to [7].

[9] A molding material containing the copolymer for suppressing protein adsorption according to any one of [1] to [7].

[10] The molding material according to [9], further containing a thermoplastic resin, in which the molding material contains 1% by mass or more of the copolymer for suppressing protein adsorption.

[11] The molding material according to [10], in which the thermoplastic resin is a (meth)acrylic resin or an olefin resin.

[12] A molded article that comes in contact with a protein, which is obtained by molding the molding material according to any one of [9] to [11].

[13] The molded article according to [12], in which the molded article is any one coming in contact with a plasma protein, which is selected from the group consisting of a medical instrument, a biochemical instrument, and a cell therapy apparatus, or any one coming in contact with a protein other than the plasma protein, which is selected from the group consisting of a petri dish for cell culture, a cell for cell culture, a microplate for cell culture, a bag for cell culture, a plate for cell culture, a tube for cell culture, a flask for cell culture, a petri dish for biopharmacy, a cell for biopharmacy, a microplate for biopharmacy, a plate for biopharmacy, a tube for biopharmacy, a bag for biopharmacy, a container for biopharmacy, a syringe for biopharmacy, a flask for biopharmacy, a petri dish for antibody drug, a cell for antibody drug, a microplate for antibody drug, a plate for antibody drug, a tube for antibody drug, a bag for antibody drug, a container for antibody drug, and a syringe for antibody drug, a flask for antibody drug, a blood bag, a vial for blood product, and a bag for blood product.

[14] A copolymer-containing composition containing the copolymer for suppressing protein adsorption according to any one of [1] to [7] and a solvent.

[15] A coating film formed by using the copolymer-containing composition according to [14].

[16] An article that comes in contact with a protein, containing the coating film according to [15] on a surface of the article, the surface coming in contact with a protein.

[17] The article having the coating film, according to [16], in which the article having the coating film is any one having the coating film on a surface thereof, where the surface comes in contact with a plasma protein, which is selected from the group consisting of a medical instrument, a biochemical instrument, and a cell therapy apparatus, or any one having the coating film on a surface thereof, where the surface comes in contact with a protein other than the plasma protein, which is selected from the group consisting of a petri dish for cell culture, a cell for cell culture, a microplate for cell culture, a bag for cell culture, a plate for cell culture, a tube for cell culture, a flask for cell culture, a petri dish for biopharmacy, a cell for biopharmacy, a microplate for biopharmacy, a plate for biopharmacy, a tube for biopharmacy, a bag for biopharmacy, a container for biopharmacy, a syringe for biopharmacy, a flask for biopharmacy, a petri dish for antibody drug, a cell for antibody drug, a microplate for antibody drug, a plate for antibody drug, a tube for antibody drug, a bag for antibody drug, a container for antibody drug, and a syringe for antibody drug, a flask for antibody drug, a blood bag, a vial for blood product, and a bag for blood product.

[18] A method for producing a copolymer, including performing suspension polymerization of a monomer mixture which contains a macromonomer (d') containing a constitutional unit (a) represented by Formula (1) and having a radically polymerizable group and a monomer (b') represented by Formula (2').

(In the formula, $R^1$ represents a hydrogen atom or a methyl group, $R^2$ is an $OR^{33}$, a halogen atom, $COR^{34}$, $COOR^{35}$, CN, $CONR^{36}R^{37}$, or $R^{38}$, where $R^{33}$ to $R^{37}$ each independently represent a hydrogen atom, a substituted or unsubstituted alkyl group, a substituted or unsubstituted alicyclic group, a substituted or unsubstituted aryl group, a substituted or unsubstituted heteroaryl group, a substituted or unsubstituted non-aromatic heterocyclic group, a substituted or unsubstituted aralkyl group (arylalkyl group), a substituted or unsubstituted alkaryl group (alkylaryl group), or a substituted or unsubstituted organosilyl group, and $R^{38}$ represents a substituted or unsubstituted aryl group or a substituted or unsubstituted heteroaryl group.)

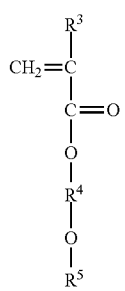

(2')

(In the formula, $R^3$ represents a hydrogen atom or a methyl group, $R^4$ represents an alkylene group having 1 to 4 carbon atoms, and $R^5$ represents a hydrocarbon group having 1 to 6 carbon atoms.)

[19] The method for producing a copolymer according to [18], in which the monomer (b') is one or more selected from the group consisting of methoxymethyl acrylate, methoxyethyl acrylate, methoxypropyl acrylate, methoxybutyl acrylate, ethoxymethyl acrylate, ethoxyethyl acrylate, ethoxypropyl acrylate, ethoxybutyl acrylate, propoxymethyl acrylate, propoxyethyl acrylate, propoxypropyl acrylate, propoxybutyl acrylate, butoxymethyl acrylate, butoxyethyl acrylate, butoxypropyl acrylate, butoxybutyl acrylate, methoxymethyl methacrylate, methoxyethyl methacrylate, methoxypropyl methacrylate, methoxybutyl methacrylate, ethoxymethyl methacrylate, ethoxyethyl methacrylate, ethoxypropyl methacrylate, ethoxybutyl methacrylate, propoxymethyl methacrylate, propoxyethyl methacrylate, propoxypropyl methacrylate, propoxybutyl methacrylate, butoxymethyl methacrylate, butoxyethyl methacrylate, butoxypropyl methacrylate, and butoxybutyl methacrylate.

[20] The method for producing a copolymer according to [18] or [19], in which a total mass of the monomer (b') present in the monomer mixture is more than a total mass of the constitutional unit (a) present in the monomer mixture.

[21] The method for producing a copolymer according to any one of [18] to [20], further including synthesizing the macromonomer (d') by a suspension polymerization method.

The present invention may have a combination of the following followings.

[1] A copolymer containing a constitutional unit (a) represented by Formula (1) and a constitutional unit (b) represented by Formula (2).

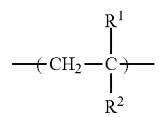

(1)

(In the formula, $R^1$ represents a hydrogen atom or a methyl group, $R^2$ is an $OR^{33}$, a halogen atom, $COR^{34}$, $COOR^{35}$, CN, $CONR^{36}R^{37}$, or $R^{38}$, where $R^{33}$ to $R^{37}$ each independently represent a hydrogen atom, a substituted or unsubstituted alkyl group, a substituted or unsubstituted alicyclic group, a substituted or unsubstituted aryl group, a substituted or unsubstituted heteroaryl group, a substituted or unsubstituted non-aromatic heterocyclic group, a substituted or unsubstituted aralkyl group (arylalkyl group), a substituted or unsubstituted alkaryl group (alkylaryl group), or a substituted or unsubstituted organosilyl group, and $R^{38}$ represents a substituted or unsubstituted aryl group or a substituted or unsubstituted heteroaryl group.)

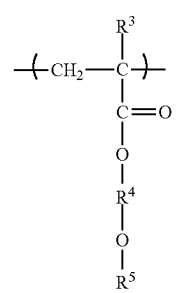

(2)

(In the formula, $R^3$ represents a hydrogen atom or a methyl group, $R^4$ represents an alkylene group having 1 to 4 carbon atoms, and $R^5$ represents a hydrocarbon group having 1 to 6 carbon atoms.)

[2] The copolymer according to [1], in which $R^4$ is a methylene group, an ethylene group, propylene group, or a butylene group.

[3] The copolymer according to [1] or [2], in which $R^5$ represents a methyl group, an ethyl group, a propyl group, a butyl group, a pentyl group, or a hexyl group.

[4] The copolymer according to any one of [1] to [3], in which the constitutional unit (a) is a constitutional unit derived from a (meth)acrylic acid ester.

[5] The copolymer according to any one of [1] to [4], containing a constitutional unit (d) derived from a macromonomer containing the constitutional unit (a).

[6] The copolymer according to [5], in which the macromonomer is represented by Formula (4).

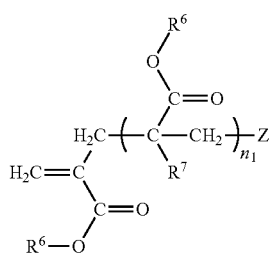

(4)

(In the formula, $R^6$'s each independently represent a hydrogen atom, an alkyl group which is unsubstituted or has a substituent, an alicyclic group which is unsubstituted or has a substituent, an aryl group which is unsubstituted or has a substituent, a heteroaryl group which is unsubstituted or has a substituent, or a non-aromatic heterocyclic group which is unsubstituted or has a substituent, where a plurality of $R^6$'s may be the same or different from each other, $R^7$'s represent a hydrogen atom or a methyl group, where a plurality of $R^7$'s may be the same or different from each other, Z is a terminal group, and $n_1$ is a natural number of 2 to 10,000.)

[7] The copolymer according to [6], in which the substituent is an alkyl group having 1 to 5 carbon atoms, an aryl group having 6 to 20 carbon atoms, or a halogen atom.

[8] The copolymer according to [6] or [7], which may differ. $R^6$'s each independently represent a hydrogen atom or a methyl group, and a plurality of $R^6$'s may be the same or different from each other, $R^7$ may represent a hydrogen atom or a methyl group, and a plurality of $R^7$'s may be the same or different from each other.

[9] The copolymer according to any one of [6] to [8], in which a number-average molecular weight (Mn) of the macromonomer is preferably 200 to 100,000, more preferably 500 to 100,000, still more preferably 1,000 to 50,000, and particularly preferably 2,000 to 50,000.

[10] The copolymer according to any one of [6] to [9], in which a molecular weight distribution of the macromonomer is preferably 1.5 to 3.0 and more preferably 2.0 to 2.5.

[11] The copolymer according to any one of [1] to [10], in which the constitutional unit (b) is derived from a monomer selected from the group consisting of methoxymethyl acrylate, methoxyethyl acrylate, methoxypropyl acrylate, methoxybutyl acrylate, ethoxymethyl acrylate, ethoxyethyl acrylate, ethoxypropyl acrylate, ethoxybutyl acrylate, propoxymethyl acrylate, propoxyethyl acrylate, propoxypropyl acrylate, propoxybutyl acrylate, butoxymethyl acrylate, butoxyethyl acrylate, butoxypropyl acrylate, butoxybutyl acrylate, methoxymethyl methacrylate, methoxyethyl methacrylate, methoxypropyl methacrylate, methoxybutyl methacrylate, ethoxymethyl methacrylate, ethoxyethyl methacrylate, ethoxypropyl methacrylate, ethoxybutyl methacrylate, propoxymethyl methacrylate, propoxyethyl methacrylate, propoxypropyl methacrylate, propoxybutyl methacrylate, butoxymethyl methacrylate, butoxyethyl methacrylate, butoxypropyl methacrylate, and butoxybutyl methacrylate.

[12] The copolymer according to any one of [1] to [11], in which the copolymer has a weight-average molecular weight (Mw) of 75,000 or more.

[13] The copolymer according to any one of [1] to [12], in which a total mass of the constitutional unit (b) is more than a total mass of the constitutional unit (a) in all constitutional units.

[14] The copolymer according to any one of [1] to [13], in which a weight-average molecular weight (Mw) is more preferably 75,000 or more and 1,000,000 or less and still more preferably 80,000 or more and 500,000 or less.

[15] The copolymer according to any one of [1] to [14], in which a proportion of the constitutional unit (b) is preferably more than 50% by mass and 95% by mass or less, more preferably more than 50% by mass and 80% by mass or less, and still more preferably more than 50% by mass and 75% by mass or less, with respect to a total mass of all constitutional units.

[16] The copolymer according to any one of [1] to [15], in which a proportion of the constitutional unit (a) is preferably 30% to 70% by mass and more preferably 40% to 60% by mass, with respect to a total mass of all constitutional units.

[17] A resin modifier made of the copolymer according to any one of [1] to [16].

[18] A molding material containing the copolymer according to any one of [1] to [16].

[19] The molding material according to [18], further containing a thermoplastic resin, in which the molding material contains 1% by mass or more of the copolymer.

[20] The molding material according to [19], in which the thermoplastic resin is a (meth)acrylic resin or an olefin resin.

[21] The molding material according to [19], in which the thermoplastic resin is a polymethyl methacrylate or an olefin resin.

[22] A molded article that comes in contact with a protein, which is obtained by molding the molding material according to any one of [18] to [21].

[23] The molded article according to [22], in which the molded article is any one coming in contact with a plasma protein, which is selected from the group consisting of a medical instrument, a biochemical instrument, and a cell therapy apparatus, or any one coming in contact with a protein other than the plasma protein, which is selected from the group consisting of a petri dish for cell culture, a cell for cell culture, a microplate for cell culture, a bag for cell culture, a plate for cell culture, a tube for cell culture, a flask for cell culture, a petri dish for biopharmacy, a cell for biopharmacy, a microplate for biopharmacy, a plate for biopharmacy, a tube for biopharmacy, a bag for biopharmacy, a container for biopharmacy, a syringe for biopharmacy, a flask for biopharmacy, a petri dish for antibody drug, a cell for antibody drug, a microplate for antibody drug, a plate for antibody drug, a tube for antibody drug, a bag for antibody drug, a container for antibody drug, and a syringe for antibody drug, a flask for antibody drug, a blood bag, a vial for blood product, and a bag for blood product.

[24] A copolymer-containing composition containing the copolymer according to any one of [1] to [16] and a solvent.

[25] The copolymer-containing composition according to [24], in which a content of the copolymer with respect to the copolymer-containing composition is preferably 1% to 85% by mass, more preferably 5% to 80% by mass, still more preferably 10% to 75% by mass, and particularly preferably 15% to 70% by mass.

[26] The copolymer-containing composition according to [24] or [25], in which a content of the solvent with respect to the copolymer-containing composition is preferably 15% to 99% by mass, more preferably 20% to 95% by mass, and particularly preferably 25% to 90% by mass.

[27] A coating film formed by using the copolymer-containing composition according to any one of [24] to [26].

[28] An article that comes in contact with a protein, containing the coating film according to [27] on a surface of the article, the surface coming in contact with a protein.

[29] An article containing the coating film according to [28], in which the article having the coating film is any one having the coating film on a surface thereof, where the surface comes in contact with a plasma protein, which is selected from the group consisting of a medical instrument, a biochemical instrument, and a cell therapy apparatus, or any one having the coating film on a surface thereof, where the surface comes in contact with a protein other than the plasma protein, which is selected from the group consisting of a petri dish for cell culture, a cell for cell culture, a microplate for cell culture, a bag for cell culture, a plate for cell culture, a tube for cell culture, a flask for cell culture, a petri dish for biopharmacy, a cell for biopharmacy, a microplate for biopharmacy, a plate for biopharmacy, a tube for biopharmacy, a bag for biopharmacy, a container for biopharmacy, a syringe for biopharmacy, a flask for biopharmacy, a petri dish for antibody drug, a cell for antibody drug, a microplate for antibody drug, a plate for antibody drug, a tube for antibody drug, a bag for antibody drug, a container for antibody drug, and a syringe for antibody drug, a flask for antibody drug, a blood bag, a vial for blood product, and a bag for blood product.

[30] A method for producing a copolymer, including performing suspension polymerization of a monomer mixture which contains a macromonomer (d') containing a constitutional unit (a) represented by Formula (1) and having a radically polymerizable group and a monomer (b') represented by Formula (2').

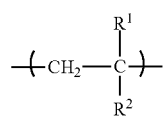
(1)

(In the formula, $R^1$ represents a hydrogen atom or a methyl group, $R^2$ is an $OR^{33}$, a halogen atom, $COR^{34}$, $COOR^{35}$, CN, $CONR^{36}R^{37}$, or $R^{38}$, where $R^{33}$ to $R^{37}$ each independently represent a hydrogen atom, a substituted or unsubstituted alkyl group, a substituted or unsubstituted alicyclic group, a substituted or unsubstituted aryl group, a substituted or unsubstituted heteroaryl group, a substituted or unsubstituted non-aromatic heterocyclic group, a substituted or unsubstituted aralkyl group, a substituted or unsubstituted alkaryl group, or a substituted or unsubstituted organosilyl group, and $R^{38}$ represents a substituted or unsubstituted aryl group or a substituted or unsubstituted heteroaryl group.)

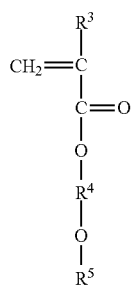
(2')

(In the formula, $R^3$ represents a hydrogen atom or a methyl group, $R^4$ represents an alkylene group having 1 to 4 carbon atoms, and $R^5$ represents a hydrocarbon group having 1 to 6 carbon atoms.)

[31] The method for producing a copolymer [30], in which the monomer (b') is one or more which are derived from a monomer selected from the group consisting of methoxymethyl acrylate, methoxyethyl acrylate, methoxypropyl acrylate, methoxybutyl acrylate, ethoxymethyl acrylate, ethoxyethyl acrylate, ethoxypropyl acrylate, ethoxybutyl acrylate, propoxymethyl acrylate, propoxyethyl acrylate, propoxypropyl acrylate, propoxybutyl acrylate, butoxymethyl acrylate, butoxyethyl acrylate, butoxypropyl acrylate, butoxybutyl acrylate, methoxymethyl methacrylate, methoxyethyl methacrylate, methoxypropyl methacrylate, methoxybutyl methacrylate, ethoxymethyl methacrylate, ethoxyethyl methacrylate, ethoxypropyl methacrylate, ethoxybutyl methacrylate, propoxymethyl methacrylate, propoxyethyl methacrylate, propoxypropyl methacrylate, propoxybutyl methacrylate, butoxymethyl methacrylate, butoxyethyl methacrylate, butoxypropyl methacrylate, and butoxybutyl methacrylate.

[32] The method for producing a copolymer according to [30] or [31], in which a total mass of the monomer (b') present in the monomer mixture is more than a total mass of the constitutional unit (a) present in the monomer mixture.

[33] The method for producing a copolymer according to any one of [30] to [32], further including synthesizing the macromonomer (d') by a suspension polymerization method.

[34] The method for producing a copolymer according to any one of [30] to [32], in which the method is for producing the copolymer according to any one of [1] to [16].

[35] The copolymer according to any one of [1] to [16], in which the copolymer is used for suppressing protein adsorption.

Advantageous Effects of Invention

The copolymer of the present invention has a protein adsorption suppressing effect and is suitable for producing an article that comes in contact with a protein.

According to the method for producing a copolymer of the present invention, a copolymer having excellent moldability and a protein adsorption suppressing effect can be obtained.

According to the resin modifier of the present invention, the protein adsorption suppressing effect of the resin composition can be improved.

According to the molding material of the present invention, a molded body having a protein adsorption suppressing effect can be produced.

The article of the present invention has a protein adsorption suppressing effect.

According to the copolymer-containing composition of the present invention, a coating film having a protein adsorption suppressing effect can be formed.

The coating film of the present invention has a protein adsorption suppressing effect.

BRIEF DESCRIPTION OF DRAWINGS

FIG. 1 is a graph showing the results of protein adsorption tests of Comparative Examples and Practical Examples.

DESCRIPTION OF EMBODIMENTS

The definitions of the following terms apply throughout the present specification and Claims.

The "(meth)acrylic monomer" means a monomer having a (meth)acryloyl group.

The "(meth)acryloyl group" is a general term for an acryloyl group and a methacryloyl group.

The "(meth)acrylate" is a general term for an acrylate and a methacrylate.

The "(meth)acrylic acid" is a general term for acrylic acid and methacrylic acid.

The "to" indicating a numerical range is used to mean that both numerical values described before and after "to" are included as a lower limit value and an upper limit value.

The "substituted or unsubstituted" means that a hydrocarbon group is "unsubstituted or has a substituent".

Hereinafter, embodiments of the present invention will be described. The following embodiments are merely exemplary to describe the present invention and are not intended to limit the present invention only to these embodiments. The present invention can be implemented in various aspects as long as it is not departed from the gist thereof.

<Copolymer for Suppressing Protein Adsorption>

A copolymer for suppressing protein adsorption of the present embodiment (hereinafter, simply referred to as a "copolymer") has a constitutional unit (a) represented by Formula (1) and a constitutional unit (b) represented by Formula (2).

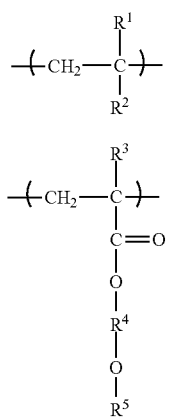

In Formula (1), $R^1$ represents a hydrogen atom or a methyl group, $R^2$ is an $OR^{33}$, a halogen atom, $COR^{34}$, $COOR^{35}$, CN, $CONR^{36}R^{37}$, or $R^{38}$, where $R^{33}$ to $R^{37}$ each independently represent a hydrogen atom, a substituted or unsubstituted alkyl group, a substituted or unsubstituted alicyclic group, a substituted or unsubstituted aryl group, a substituted or unsubstituted heteroaryl group, a substituted or unsubstituted non-aromatic heterocyclic group, a substituted or unsubstituted aralkyl group, a substituted or unsubstituted alkaryl group, or a substituted or unsubstituted organosilyl group, and $R^{38}$ represents a substituted or unsubstituted aryl group or a substituted or unsubstituted heteroaryl group.

In Formula (2), $R^3$ represents a hydrogen atom or a methyl group, $R^4$ represents an alkylene group having 1 to 4 carbon atoms, and $R^5$ represents a hydrocarbon group having 1 to 6 carbon atoms.

The copolymer may be a random copolymer, but from the viewpoint of suppressing protein adsorption, preferably has a structure of a block copolymer or graft copolymer, which has a polymer chain (3A) of the constitutional unit (a), where the polymer chain (3A) is represented by Formula (3A), and a polymer chain (3B) of the constitutional unit (b), where the polymer chain (3A) is represented by Formula (3B).

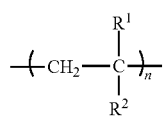

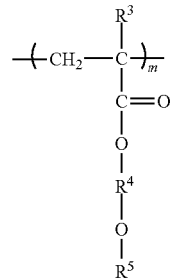

$R^1$ and $R^2$ in Formula (3A) are each the same as $R^1$ and $R^2$ in Formula (1). n is a natural number of 1 to 1,000,000. From the viewpoint of suppressing protein adsorption, n is preferably 2 to 1,000, more preferably 5 to 1,000, still more preferably 10 to 500, and particularly preferably 20 to 500.

$R^3$ to $R^5$ in Formula (3B) are each the same as $R^3$ to $R^5$ in Formula (2). m is a natural number of 1 to 1,000,000. From the viewpoint of suppressing protein adsorption, m is preferably 2 to 100,000 and more preferably 5 to 50,000. Further, in a case where m is equal to or more than the lower limit value, the protein adsorption suppressing effect is more excellent, and in a case where m is equal to or less than the upper limit value, the moldability is more excellent.

In a case where two or more polymer chains (3A) are present in one molecule of the copolymer, the polymerization degrees (n) of polymer chains (3A) may be the same or different from each other.

In a case where two or more polymer chains (3B) are present in one molecule of the copolymer, the polymerization degrees (m) of polymer chains (3B) may be the same or different from each other.

<Constitutional Unit (a)>

The constitutional unit (a) has a structure represented by Formula (1).

The constitutional unit (a) is preferably a constitutional unit derived from a (meth)acrylic acid ester.

$R^1$ is preferably a hydrogen atom or a methyl group, and $R^2$ is preferably $COOR^{35}$.

Examples of the unsubstituted alkyl group of $R^{33}$ to $R^{37}$ include a branched or linear alkyl group having 1 to 22 carbon atoms. Specific examples of the branched or linear alkyl groups having 1 to 22 carbon atoms include a methyl group, an ethyl group, an n-propyl group, an i-propyl group, an n-butyl group, a t-butyl group, an i-butyl group, a pentyl group (an amyl group), an i-pentyl group, a hexyl group, a heptyl group, a 2-ethylhexyl group, an octyl group, an i-octyl group, a nonyl group, an i-nonyl group, a decyl group, an i-decyl group, an undecyl group, a dodecyl group (a lauryl group), a tridecyl group, a tetradecyl group, a pentadecyl group, a hexadecyl group, a heptadecyl group, an octadecyl group (a stearyl group), an i-octadecyl group, a nonadecil group, an icosyl group, and a docosyl group.

The unsubstituted alicyclic group of $R^{33}$ to $R^{37}$ may be a monocyclic group or a polycyclic group, and examples thereof include an alicyclic group having 3 to 20 carbon atoms. The alicyclic group is preferably a saturated alicyclic group, and specific examples thereof include a cyclopropyl group, a cyclobutyl group, a cyclopentyl group, a cyclohexyl group, a cycloheptyl group, a bicyclo[2.2.1]heptyl group, a cyclooctyl group, and an adamantyl group.

Examples of the unsubstituted aryl group of $R^{33}$ to $R^{37}$ include an aryl group having 6 to 18 carbon atoms. Specific examples of the aryl group having 6 to 18 carbon atoms include a phenyl group and a naphthyl group.

Examples of the unsubstituted heteroaryl group of $R^{33}$ to $R^{37}$ include a heteroaryl group having 4 to 18 carbon atoms. Specific examples of the heteroaryl group having 4 to 18 carbon atoms include a pyridyl group and a carbazolyl group.

Examples of the unsubstituted non-aromatic heterocyclic group of $R^{33}$ to $R^{37}$ include a heterocyclic group having 4 to 18 carbon atoms. Specific examples of the heterocyclic group having 4 to 18 carbon atoms include oxygen atom-containing heterocyclic groups such as a tetrahydrofuryl group and a tetrahydropyranyl group, and nitrogen atom-containing heterocyclic groups such as a γ-butyrolactone group, an ε-caprolactone group, a pyrrolidinyl group, a pyrrolidone group, and a morpholino group.

Examples of the unsubstituted aralkyl group of $R^{33}$ to $R^{37}$ include a benzyl group and a phenylethyl group.

Examples of the unsubstituted organosilyl group of $R^{33}$ to $R^{37}$ include —$SiR^{17}R^{18}R^{19}$ (here, $R^{17}$ to $R^{19}$ each independently represent a substituted or unsubstituted alkyl group, a substituted or unsubstituted alicyclic group, or a substituted or unsubstituted aryl group).

Examples of the substituted or unsubstituted alkyl group in $R^{17}$ to $R^{19}$ include the same groups as described above, and examples thereof include a methyl group, an ethyl group, an n-propyl group, an n-butyl group, an n-amyl group, an n-hexyl group, an n-octyl group, an n-dodecyl group, a stearyl group, a lauryl group, an isopropyl group, an isobutyl group, an s-butyl group, a 2-methylisopropyl group, and a benzyl group.

Examples of the substituted or unsubstituted alicyclic group in $R^{17}$ to $R^{19}$ include the same groups as described above, and examples thereof include a cyclohexyl group.

Examples of the substituted or unsubstituted aryl group in $R^{17}$ to $R^{19}$ include the same groups as described above, and examples thereof include a phenyl group and a p-methylphenyl.

$R^{17}$ to $R^{19}$ may be the same or different from each other.

Examples of the substituent of $R^{33}$ to $R^{37}$ include equal to or more than one selected from the group consisting of an alkyl group (however, a case where $R^{33}$ to $R^{37}$ are an alkyl group having a substituent is excluded), an aryl group, —$COOR^{11}$, a cyano group, —$OR^{12}$, —$NR^{13}R^{14}$, —$CONR^{15}R^{16}$, a halogen atom, an allyl group, an epoxy group, a siloxy group, and a group exhibiting hydrophilicity or ionicity.

Here, $R^{11}$ to $R^{16}$ each independently represent a hydrogen atom, a substituted or unsubstituted alkyl group, a substituted or unsubstituted alicyclic group, or a substituted or unsubstituted aryl group).

Examples of the alkyl group and the aryl group in the substituent described above include the same groups as those each described as the unsubstituted alkyl group and the unsubstituted aryl group.

$R^{11}$ of —$COOR^{11}$ in the substituent described above is preferably a hydrogen atom or an unsubstituted alkyl group. That is, —$COOR^{11}$ is preferably a carboxy group or an alkoxycarbonyl group. Examples of the alkoxycarbonyl group include a methoxycarbonyl group.

The $R^{12}$ of —$OR^{12}$ in the substituent described above is preferably a hydrogen atom or an unsubstituted alkyl group. That is, —$OR^{12}$ is preferably a hydroxy group or an alkoxy group. Examples of the alkoxy group include an alkoxy group having 1 to 12 carbon atoms, and specific examples thereof include a methoxy group.

Examples of the —$NR^{13}R^{14}$ in the substituent described above include an amino group, a monomethylamino group, and a dimethylamino group.

Examples of the —$CONR^{15}R^{16}$ in the substituent described above include a carbamoyl group (—$CONH_2$), an N-methylcarbamoyl group (—$CONHCH_3$), and an N,N-dimethylcarbamoyl group (a dimethylamide group: —$CON(CH_3)_2$).

Examples of the halogen atom in the substituent described above include a fluorine atom, a chlorine atom, a bromine atom, and an iodine atom.

Examples of the group exhibiting hydrophilicity or ionicity in the substituent described above include an alkali salt of a carboxy group or an alkali salt of a sulfo group, a poly(alkylene oxide) group such as a polyethylene oxide group or a polypropylene oxide group, and a cationic substituent such as a quaternary ammonium base.

Examples of the constitutional unit (a) represented by Formula (1) include a constitutional unit derived from a polymerizable monomer (a').

Examples of the polymerizable monomer (a') include hydrocarbon group-containing (meth)acrylic acid esters such as methyl (meth)acrylate, ethyl (meth)acrylate, n-propyl (meth)acrylate, isopropyl (meth)acrylate, n-butyl (meth) acrylate, isobutyl (meth)acrylate, t-butyl (meth)acrylate, iso-amyl (meth)acrylate, hexyl (meth)acrylate, 2-ethylhexyl (meth)acrylate, octyl (meth)acrylate, isooctyl (meth)acrylate, nonyl (meth)acrylate, isononyl (meth)acrylate, decyl (meth)acrylate, isodecyl (meth)acrylate, lauryl (meth)acrylate, hexadecyl (meth)acrylate, stearyl (meth)acrylate, isostearyl (meth)acrylate, phenyl (meth)acrylate, benzyl (meth)acrylate, cyclohexyl (meth)acrylate, tetrahydrofurfuryl (meth)acrylate, isobornyl (meth)acrylate, 3,5,5-trimethylcyclohexyl (meth)acrylate, dicyclopentanyl (meth)acrylate, dicyclopentenyl (meth)acrylate, dicyclopentenyloxyethyl (meth)acrylate, terpene acrylate and a derivative thereof, a hydrogenated rosin acrylate and a derivative thereof, and docosyl (meth)acrylate;

hydroxyl group-containing (meth)acrylic acid esters such as 2-hydroxyethyl (meth)acrylate, 2-hydroxypropyl (meth)acrylate, 2-hydroxybutyl (meth)acrylate, 3-hydroxybutyl (meth)acrylate, 4-hydroxybutyl (meth) acrylate, and glycerol (meth)acrylate;

carboxyl group-containing vinyl-based monomers such as (meth)acrylic acid, 2-(meth)acryloyloxyethyl hexahydrophthalic acid, 2-(meth)acryloyloxypropyl hexahydrophthalic acid, 2-(meth)acryloyloxyethyl phthalic acid, 2-(meth)acryloyloxy propylphthalic acid, 2-(meth)acryloyloxyethyl maleic acid, 2-(meth)acryloyloxypropyl maleic acid, 2-(meth)acryloyloxyethyl succinic acid, 2-(meth)acryloyloxypropyl succinic acid, crotonic acid, fumaric acid, maleic acid, itaconic acid, citraconic acid, monomethyl maleate, monoethyl maleate, monooctyl maleate, monomethyl itaconate, monoethyl itaconate, monobutyl itaconate, monooctyl itaconate, monomethyl fumarate, monoethyl fumarate, monobutyl fumarate, monooctyl fumarate, and monoethyl citraconate;

acid anhydride group-containing vinyl-based monomers such as maleic anhydride and itaconic anhydride;

unsaturated dicarboxylic acid diester monomers such as dimethyl malate, dibutyl malate, dimethyl fumarate, dibutyl fumarate, and dibutyl itaconate, diperfluorocyclohexyl fumarate;

epoxy group-containing vinyl-based monomers such as glycidyl (meth)acrylate, glycidyl α-ethyl acrylate, and 3,4-epoxybutyl (meth)acrylate;

amino group-containing (meth)acrylic acid ester-based vinyl monomers such as dimethylaminoethyl (meth)acrylate and diethylaminoethyl (meth)acrylate;

vinyl-based monomers containing an amide group, such as (meth)acrylamide, dimethyl (meth)acrylamide, diethyl (meth)acrylamide, N-t-butyl (meth)acrylamide, N-methylol (meth)acrylamide, N-isopropyl acrylamide, hydroxyethyl acrylamide, N-methoxymethyl (meth)acrylamide, N-butoxymethyl (meth)acrylamide, diacetone acrylamide, maleic acid amide, and maleimide;

vinyl-based monomers such as styrene, α-methyl styrene, vinyl toluene, (meth)acrylonitrile, vinyl chloride, vinyl acetate, and vinyl propionate;

polyfunctional vinyl-based monomers such as divinyl benzene, ethylene glycol di(meth)acrylate, 1,3-butylene glycol di(meth)acrylate, 1,4-butanediol di(meth)acrylate, 1,6-hexanediol di(meth)acrylate, diethylene glycol di(meth)acrylate, triethylene glycol di(meth)acrylate, tetraethylene glycol di(meth)acrylate, polyethylene glycol di(meth)acrylate, tripropylene glycol di(meth)acrylate, neopentyl glycol di(meth)acrylate, 1,9-nonandiol di(meth)acrylate, 1,10-decanediol di(meth)acrylate, trimethylolpropane tri(meth)acrylate, pentaerythritol tetra(meth)acrylate, dipentaerythritol hexa(meth)acrylate, allyl (meth)acrylate, triallyl cyanurate, diallyl maleate, polypropylene glycol diallyl ether, and N,N'-methylene bis(meth)acrylamide;

heterocyclic ring-based monomers such as (meth)acryloyl morpholine, vinyl pyrrolidone, vinyl pyridine, and vinyl carbazole;

glycol ester-based monomers such as polyethylene glycol (meth)acrylate, polypropylene glycol (meth)acrylate, methoxyethyl (meth)acrylate, ethoxyethyl (meth)acrylate, n-butoxyethyl (meth)acrylate, isobutoxyethyl (meth)acrylate, t-butoxyethyl (meth)acrylate, ethoxyethoxyethyl (meth)acrylate, phenoxyethyl (meth)acrylate, nonylphenoxyethyl (meth)acrylate, 3-methoxybutyl (meth)acrylate, acetoxyethyl (meth)acrylate, "PLAXEL FM" (a caprolactone-added monomer manufactured by Daicel Corporation, trade name), "BLEMMER PME-100" (methoxypolyethylene glycol methacrylate (having two ethylene glycol chains) manufactured by NOF Corporation, trade name), "BLEMMER PME-200" (methoxypolyethylene glycol methacrylate (having four ethylene glycol chains) manufactured by NOF Corporation, trade name), "BLEMMER PME-400" (methoxypolyethylene glycol methacrylate (having nine ethylene glycol chains) manufactured by NOF Corporation, trade name), "BLEMMER 50 POEP-800B" (manufactured by NOF Corporation, octoxypolyethylene glycol-polypropylene glycol-methacrylate (having eight ethylene glycol chains and six propylene glycol chains), trade name), "BLEMMER 20 ANEP-600" (nonylphenoxy(ethylene glycol-polypropylene glycol) monoacrylate manufactured by NOF Corporation, trade name), "BLEMMER AME-100" (manufactured by NOF Corporation, trade name), "BLEMMER AME-200" (manufactured by NOF Corporation, trade name), and "BLEMMER 50 AOEP-800B" (manufactured by NOF Corporation, trade name), silane coupling agent-containing monomers such as 3-(meth)acryloxypropyl trimethoxysilane, 3-(meth)acryloxypropylmethyl diethoxysilane, 3-(meth)acryloxypropyl triethoxysilane, 3-acryloxypropyl trimethoxysilane, vinyl trimethoxysilane, and vinyl triethoxysilane, organosilyl group-containing monomers other than the silane coupling agent-containing monomers, such as trimethylsilyl (meth)acrylate, triethylsilyl (meth)acrylate, tri-n-propylsilyl (meth)acrylate, tri-n-butylsilyl (meth)acrylate, tri-n-amylsilyl (meth)acrylate, tri-n-hexylsilyl (meth)acrylate, tri-n-octylsilyl (meth)acrylate, tri-n-dodecylsilyl (meth)acrylate, triphenylsilyl (meth)acrylate, tri-p-methylphenylsilyl (meth)acrylate, tribenzylsilyl (meth)acrylate, triisopropylsilyl (meth)acrylate, triisobutylsilyl (meth)acrylate, tri-s-butylsilyl (meth)acrylate, tri-2-methylisopropylsilyl (meth)acrylate, tri-t-butylsilyl (meth)acrylate, ethyldimethylsilyl (meth)acrylate, n-butyldimethylsilyl (meth)acrylate, diisopropyl-n-butylsilyl (meth)acrylate, n-octyldi-n-butylsilyl (meth)acrylate, diisopropylstearylsilyl (meth)acrylate, dicyclohexylphenylsilyl (meth)acrylate, t-butyldiphenylsilyl (meth)acrylate, lauryldiphenylsilyl (meth)acrylate, triisopropylsilylmethyl malate, triisopropylsilylamyl malate, tri-n-butylsilyl-n-butyl malate, t-butyldiphenylsilylmethyl malate, t-butyldiphenylsilyl-n-butyl malate, triisopropylsilylmethyl fumarate, triisopropylsilylamyl fumarate, tri-n-butylsilyl-n-butyl fumarate, t-butyldiphenylsilylmethyl fumarate, t-butyldiphenylsilyl-n-butyl fumarate, Silaplane FM-0711 (manufactured by JNC corporation, trade name), Silaplane FM-0721 (manufactured by JNC corporation, trade name), Silaplane FM-0725 (manufactured by JNC corporation, trade name), Silaplane TM-0701 (manufactured by JNC corporation, trade name), Silaplane TM-0701T (manufactured by JNC corporation, trade name), X-22-174ASX (manufactured by Shin-Etsu Chemical Co., Ltd., trade name), X-22-174BX (manufactured by Shin-Etsu Chemical Co., Ltd., trade name), KF-2012 (manufactured by Shin-Etsu Chemical Co., Ltd., trade name), X-22-2426 (manufactured by Shin-Etsu Chemical Co., Ltd., trade name), and X-22-2404 (manufactured by Shin-Etsu Chemical Co., Ltd., trade name);

halogenated olefins such as vinyl chloride, vinylidene chloride, vinyl fluoride, vinylidene fluoride, and chlorotrifluoroethylene, fluorine-containing monomers (however, the halogenated olefins are excluded) such as 2-isocyanatoethyl (meth)acrylate, 2,2,2-trifluoroethyl (meth)acrylate, 2,2,3,3,3-pentafluorophenyl (meth)acrylate, 2-(perfluorobutyl)ethyl (meth)acrylate, 3-(perfluorobutyl)-2-hydroxypropyl (meth)acrylate, 2-(perfluorohexyl)ethyl (meth)acrylate, 3-perfluorohexyl-2-hydroxypropyl (meth)acrylate, 3-(perfluoro-3-methylbutyl)-2-hydroxypropyl (meth)acrylate, 2,2,3,3-tetrafluoropropyl (meth)acrylate, 1H,1H,5H-octafluoropentyl (meth)acrylate, 1H,1H,5H-octafluoropentyl (meth)methacrylate, 1H,1H,2H,2H-tridecafluorooctyl (meth)acrylate, 1H-1-(trifluoromethyl)trifluoroethyl (meth)acrylate, 1H,1H,3H-hexafluorobutyl (meth)acrylate, and 1,2,2,2-tetrafluoro-1-(trifluoromethyl)ethyl (meth)acrylate, monomers having an acetal structure such as 1-butoxyethyl (meth)acrylate, 1-(2-ethylhexyloxy)ethyl (meth)acrylate, 1-(cyclohexyloxy)ethyl methacrylate, and 2-tetrahydropyranyl (meth)acrylate, 4-methacryloyloxybenzophenone, and -2-isocyanatoethyl (meth)acrylate.

These polymerizable monomers (a') may be used alone or in a combination of two or more thereof.

The polymerizable monomer (a') is preferably a (meth) acrylic acid ester, more preferably a hydrocarbon group-containing (meth)acrylic acid ester, and particularly preferably methyl (meth)acrylate, in terms of copolymerizability.

<Macromonomer (d')>

The copolymer of the present embodiment may contain a constitutional unit (d') derived from a macromonomer containing the constitutional unit (a). The repeating unit constituting the macromonomer (d') may be only the constitutional unit (a). The macromonomer means one having a polymerizable functional group.

The macromonomer (d') preferably has the constitutional unit (a) and a radically polymerizable group.

In a case where the macromonomer (d') has a radically polymerizable group, the macromonomer (d') and the monomer (b') are copolymerized by radical polymerization to produce the copolymer of the present embodiment.

The radically polymerizable group contained in the macromonomer (d') is preferably a group having an ethylenic unsaturated bond. Examples of the group having an ethylenic unsaturated bond include $CH_2=C(COOR^6)-CH_2-$, a (meth)acryloyl group, a 2-(hydroxymethyl)acryloyl group, and a vinyl group.

Here, $R^6$ represents a hydrogen atom, an alkyl group which is unsubstituted or has a substituent, an alicyclic group which is unsubstituted or has a substituent, an aryl group which is unsubstituted or has a substituent, a heteroaryl group which is unsubstituted or has a substituent, or a non-aromatic heterocyclic group which is unsubstituted or has a substituent.

Specific examples of the unsubstituted alkyl group, the unsubstituted alicyclic group, the unsubstituted aryl group, the unsubstituted heteroaryl group, and the unsubstituted non-aromatic heterocyclic group, as $R^6$, and the substituent of each group include the same group as $R^{35}$ of $COOR^{35}$ as $R^2$ in Formula (1).

$R^6$ is preferably an alkyl group which is unsubstituted or has a substituent, or an alicyclic group which is unsubstituted or has a substituent, and more preferably an unsubstituted alkyl group or an alicyclic group which is unsubstituted or has an alkyl group as a substituent.

Among the above, in terms of the easiness of availability, a methyl group, an ethyl group, an n-propyl group, an i-propyl group, an n-butyl group, a t-butyl group, a pentyl group, a hexyl group, a heptyl group, an octyl group, a cyclopropyl group, a cyclobutyl group, an isobornyl group, or an adamantyl group is preferable, and a methyl group, an ethyl group, an n-propyl group, an i-propyl group, an n-butyl group, a t-butyl group, a cyclopropyl group, a cyclobutyl group, an isobornyl group, or an adamantyl group is more preferable.

The macromonomer (d') preferably has two or more constitutional units derived from a monomer having a radically polymerizable group.

The macromonomer (d') preferably has two or more constitutional units (a). The macromonomer (d') preferably has one or more polymer chains represented by Formula (3A). The macromonomer (d') is more preferably one having the structure of Formula (4).

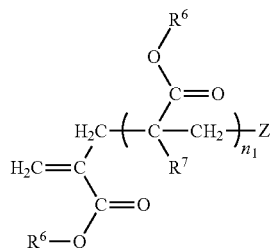

(4)

In Formula (4), $R^6$'s each independently represent a hydrogen atom, an alkyl group which is unsubstituted or has a substituent, an alicyclic group which is unsubstituted or has a substituent, an aryl group which is unsubstituted or has a substituent, a heteroaryl group which is unsubstituted or has a substituent, or a non-aromatic heterocyclic group which is unsubstituted or has a substituent, where a plurality of $R^6$'s may be the same or different from each other, $R^7$'s represent a hydrogen atom or a methyl group, where a plurality of $R^7$'s may be the same or different from each other, Z is a terminal group, and $n_1$ is a natural number of 2 to 10,000.

Examples of Z include a hydrogen atom, a group derived from a radical polymerization initiator, and a radically polymerizable group, as in the case of the terminal group of the polymer obtained by a conventionally known radical polymerization.

$n_1$ is 2 to 10,000, and from the viewpoint of moldability, is preferably 2 to 1,000, more preferably 5 to 1,000, still more preferably 10 to 500, and particularly preferably 20 to 500.

Z is the terminal group of the macromonomer (d'). Examples of Z include a hydrogen atom, a group derived from a radical polymerization initiator, and a radically polymerizable group, as in the case of the terminal group of the polymer obtained by a conventionally known radical polymerization.

$R^6$ in Formula (4) is the same as $R^6$ of $CH_2=C(COOR^6)-CH_2-$, which is a group having an ethylenic unsaturated bond.

From the viewpoint of maintaining hydrophobicity, $R^6$ in the copolymer is preferably an alkyl group, an alicyclic group, an aryl group, a heteroaryl group, or a non-aromatic heterocyclic group, more preferably an alkyl group or an alicyclic group, and particularly preferably an alkyl group.

The number-average molecular weight (Mn) of the macromonomer (d') is preferably 200 to 100,000, more preferably 500 to 100,000, still more preferably 1,000 to 50,000, and further still more preferably 2,000 to 50,000.

In a case where the number-average molecular weight (Mn) of the macromonomer (d') is equal to or more than the lower limit value, the coating film performance is more excellent, and in a case where in is equal to or less than the upper limit value, the moldability is more excellent.

The number-average molecular weight of the macromonomer (d') is measured by gel permeation chromatography (GPC) using polystyrene as a reference resin.

From the viewpoint of coating film performance, the proportion of the constitutional unit (a) to the total (100% by mass) of all the constitutional units constituting the macromonomer (d') is preferably 40% by mass or more, more preferably 50% by mass or more, and particularly preferably 100% by mass.

<Constitutional Unit (b)>

The constitutional unit (b) has a structure represented by Formula (2).

The constitutional unit (b) is a constitutional unit derived from the monomer (b') represented by Formula (2'). $R^3$, $R^4$, and $R^5$ in Formula (2') are each the same as $R^3$, $R^4$, and $R^5$ in Formula (2).

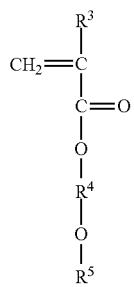

(2')

Examples of the monomer (b') include the followings; methoxymethyl acrylate, methoxyethyl acrylate, methoxypropyl acrylate, methoxybutyl acrylate, ethoxymethyl acrylate, ethoxyethyl acrylate, ethoxypropyl acrylate, ethoxybutyl acrylate, propoxymethyl acrylate, propoxyethyl acrylate, propoxypropyl acrylate, propoxybutyl acrylate, butoxymethyl acrylate, butoxyethyl acrylate, butoxypropyl acrylate, butoxybutyl acrylate, methoxymethyl methacrylate, methoxyethyl methacrylate, methoxypropyl methacrylate, methoxybutyl methacrylate, ethoxymethyl methacrylate, ethoxyethyl methacrylate, ethoxypropyl methacrylate, ethoxybutyl methacrylate, propoxymethyl methacrylate, propoxyethyl methacrylate, propoxypropyl methacrylate, propoxybutyl methacrylate, butoxymethyl methacrylate, butoxyethyl methacrylate, butoxypropyl methacrylate, and butoxybutyl methacrylate, "BLEMMER PME-100" (methoxypolyethylene glycol methacrylate (having two ethylene glycol chains) manufactured by NOF Corporation, trade name)), and "BLEMMER PME-200" (methoxypolyethylene glycol methacrylate (having four ethylene glycol chains) manufactured by NOF Corporation, trade name)).

Among them, a methoxyalkyl (meth)acrylate such as a methoxymethyl acrylate, a methoxyethyl acrylate, a methoxypropyl acrylate, a methoxybutyl acrylate, a methoxymethyl methacrylate, a methoxyethyl methacrylate, a methoxypropyl methacrylate, or a methoxybutyl methacrylate is preferable, and a methoxyethyl acrylate or a methoxyethyl methacrylate is particularly preferable, from the viewpoint of suppressing protein adsorption.

The reason why the constitutional unit (b) has the protein adsorption suppressing ability is considered as follows. As the water that hydrates the surface of a polymer, free water that weakly interacts with the polymer, intermediate water that intermediately interacts with the polymer, and antifreeze water that strongly interacts with the polymer are known. It is presumed that in a case where intermediate water is present on the surface of a polymer, a protein is difficult to adsorb to the surface of the polymer, and as a result, the protein adsorption suppressing ability is imparted. In order for the intermediate water to be present on the surface of the polymer, it is presumed to effective to contain a constitutional unit derived from the monomer (b') represented by Formula (2'), among which a constitutional unit based on methoxyethyl acrylate or methoxyethyl methacrylate is presumed to be particularly effective.

<Constitutional Unit (c)>

The copolymer of the present embodiment preferably contains a constitutional unit (c) having a structure represented by Formula (5).

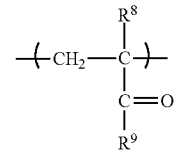

(5)

In Formula (5), $R^8$ represents a hydrogen atom or a methyl group, $R^9$ is a hydrogen atom, a halogen atom, OH, $OR^{35}$, CN, $NR^{20}R^{21}$, or $R^{22}$, where $R^{20}$, $R^{21}$, and $OR^{35}$ each independently represent a hydrogen atom, a substituted or unsubstituted alkyl group, a substituted or unsubstituted alicyclic group, a substituted or unsubstituted aryl group, a substituted or unsubstituted heteroaryl group, a substituted or unsubstituted non-aromatic heterocyclic group, a substituted or unsubstituted aralkyl group, a substituted or unsubstituted alkaryl group, or a substituted or unsubstituted organosilyl group, and $R^{22}$ represents a substituted or unsubstituted aryl group or a substituted or unsubstituted heteroaryl group.

Examples of the constitutional unit (c) include constitutional units derived from the following polymerizable monomers (c'):

hydrocarbon group-containing (meth)acrylic acid esters such as methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, isoamyl (meth)acrylate, hexyl (meth)acrylate, 2-ethylhexyl (meth)acrylate, octyl (meth)acrylate, isooctyl (meth)acrylate, nonyl (meth)acrylate, isononyl (meth)acrylate, decyl (meth)acrylate, isodecyl (meth)acrylate, lauryl (meth)acrylate, hexadecyl (meth)acrylate, stearyl (meth)acrylate, isostearyl (meth)acrylate, phenyl (meth)acrylate, benzyl (meth) acrylate, cyclohexyl (meth)acrylate, tetrahydrofurfuryl (meth)acrylate, isobornyl (meth)acrylate, 3,5,5-trimethylcyclohexyl (meth)acrylate, dicyclopentanyl (meth)acrylate, dicyclopentenyl (meth)acrylate, dicyclopentenyloxyethyl (meth)acrylate, terpene acrylate and a derivative thereof, a hydrogenated rosin acrylate and a derivative thereof, and docosyl (meth)acrylate;

hydroxyl group-containing (meth)acrylic acid esters such as 2-hydroxyethyl (meth)acrylate, 2-hydroxypropyl (meth)acrylate, 2-hydroxybutyl (meth)acrylate, 3-hydroxybutyl (meth)acrylate, 4-hydroxybutyl (meth) acrylate, and glycerol (meth)acrylate;

carboxyl group-containing vinyl-based monomers such as 2-(meth)acryloyloxyethyl hexahydrophthalic acid, 2-(meth)acryloyloxypropyl hexahydrophthalic acid, 2-(meth)acryloyloxyethyl phthalic acid, 2-(meth)acryloyloxy propylphthalic acid, 2-(meth)acryloyloxyethyl maleic acid, 2-(meth)acryloyloxypropyl maleic acid, 2-(meth)acryloyloxyethyl succinic acid, 2-(meth)acryloyloxypropyl succinic acid, (meth)acrylic acid, crotonic acid, fumaric acid, maleic acid, itaconic acid, citraconic acid, monomethyl maleate, monoethyl maleate, monooctyl maleate, monomethyl itaconate, monoethyl itaconate, monobutyl itaconate, monooctyl itaconate, monomethyl fumarate, monoethyl fumarate, monobutyl fumarate, monooctyl fumarate, and monoethyl citraconate;

acid anhydride group-containing vinyl-based monomers such as maleic anhydride and itaconic anhydride;

unsaturated dicarboxylic acid diester monomers such as dimethyl malate, dibutyl malate, dimethyl fumarate, dibutyl fumarate, and dibutyl itaconate, diperfluorocyclohexyl fumarate;

epoxy group-containing vinyl-based monomers such as glycidyl (meth)acrylate, glycidyl α-ethyl acrylate, and 3,4-epoxybutyl (meth)acrylate;

amino group-containing (meth)acrylic acid ester-based vinyl monomers such as dimethylaminoethyl (meth)acrylate and diethylaminoethyl (meth)acrylate;

vinyl-based monomers containing an amide group, such as (meth)acrylamide, N-methyl (meth)acrylamide, N,N'-dimethyl (meth)acrylamide, N-isopropyl acrylamide, N-(hydroxymethyl) acrylamide, diethyl (meth)acrylamide, hydroxyethyl acrylamide, N-butoxymethyl (meth)acrylamide, diacetone acrylamide, maleic acid amide, and maleimide;

polyfunctional vinyl-based monomers such as ethylene glycol di(meth)acrylate, 1,3-butylene glycol di(meth)acrylate, 1,4-butanediol di(meth)acrylate, 1,6-hexanediol di(meth)acrylate, diethylene glycol di(meth)acrylate, triethylene glycol di(meth)acrylate, tetraethylene glycol di(meth)acrylate, polyethylene glycol di(meth)acrylate, tripropylene glycol di(meth)acrylate, neopentyl glycol di(meth)acrylate, 1,9-nonandiol di(meth)acrylate, 1,10-decanediol di(meth)acrylate, trimethylolpropane tri(meth)acrylate, pentaerythritol tetra(meth)acrylate, dipentaerythritol hexa(meth)acrylate, allyl (meth)acrylate, triallyl cyanurate, diallyl maleate, polypropylene glycol diallyl ether, and N,N'-methylene bis(meth)acrylamide;

heterocyclic ring-based monomers such as (meth)acryloyl morpholine, vinyl pyrrolidone, vinyl pyridine, and vinyl carbazole;

polyethylene glycol (meth)acrylate, polypropylene glycol (meth)acrylate, phenoxyethyl (meth)acrylate, nonylphenoxyethyl (meth)acrylate, acetoxyethyl (meth)acrylate, "PLAXEL FM" (a caprolactone-added monomer manufactured by Daicel Corporation, trade name), silane coupling agent-containing monomers such as 3-(meth)acryloxypropyl trimethoxysilane, 3-(meth)acryloxypropylmethyl diethoxysilane, 3-(meth)acryloxypropyl triethoxysilane, 3-acryloxypropyl trimethoxysilane, vinyl trimethoxysilane, and vinyl triethoxysilane, organosilyl group-containing monomers other than the silane coupling agent-containing monomers, such as trimethylsilyl (meth)acrylate, triethylsilyl (meth)acrylate, tri-n-propylsilyl (meth)acrylate, tri-n-butylsilyl (meth)acrylate, tri-n-amylsilyl (meth)acrylate, tri-n-hexylsilyl (meth)acrylate, tri-n-octylsilyl (meth)acrylate, tri-n-dodecylsilyl (meth)acrylate, triphenylsilyl (meth)acrylate, tri-p-methylphenylsilyl (meth)acrylate, tribenzylsilyl (meth)acrylate, triisopropylsilyl (meth)acrylate, triisobutylsilyl (meth)acrylate, tri-s-butylsilyl (meth)acrylate, tri-2-methylisopropylsilyl (meth)acrylate, tri-t-butylsilyl (meth)acrylate, ethyldimethylsilyl (meth)acrylate, n-butyldimethylsilyl (meth)acrylate, diisopropyl-n-butylsilyl (meth)acrylate, n-octyldi-n-butylsilyl(meth)acrylate, diisopropylstearylsilyl (meth)acrylate, dicyclohexylphenylsilyl (meth)acrylate, t-butyldiphenylsilyl (meth)acrylate, lauryldiphenylsilyl (meth)acrylate, triisopropylsilylmethyl malate, triisopropylsilylamyl malate, tri-n-butylsilyl-n-butyl malate, t-butyldiphenylsilylmethyl malate, t-butyldiphenylsilyl-n-butyl malate;

fluorine-containing monomers (however, the halogenated olefins are excluded) such as 2-isocyanatoethyl (meth)acrylate, 2,2,2-trifluoroethyl (meth)acrylate, 2,2,3,3,3-pentafluorophenyl (meth)acrylate, 2-(perfluorobutyl)ethyl (meth)acrylate, 3-(perfluorobutyl)-2-hydroxypropyl (meth)acrylate, 2-(perfluorohexyl)ethyl (meth)acrylate, 3-perfluorohexyl-2-hydroxypropyl (meth)acrylate, 3-(perfluoro-3-methylbutyl)-2-hydroxypropyl (meth)acrylate, 2,2,3,3-tetrafluoropropyl (meth)acrylate, 1H,1H,5H-octafluoropentyl (meth)acrylate, 1H,1H,5H-octafluoropentyl (meth)methacrylate, 1H,1H,2H,2H-tridecafluorooctyl (meth)acrylate, 1H-1-(trifluoromethyl)trifluoroethyl (meth)acrylate, 1H,1H,3H-hexafluorobutyl (meth)acrylate, and 1,2,2,2-tetrafluoro-1-(trifluoromethyl)ethyl (meth)acrylate, monomers having an acetal structure such as 1-butoxyethyl (meth)acrylate, 1-(2-ethylhexyloxy)ethyl (meth)acrylate, 1-(cyclohexyloxy)ethyl methacrylate, and 2-tetrahydropyranyl (meth)acrylate, 4-methacryloyloxybenzophenone, and -2-isocyanatoethyl (meth)acrylate.

Among them, from the viewpoint of easiness of handling, the following is preferable:

hydrocarbon group-containing (meth)acrylic acid esters such as methyl (meth)acrylate, ethyl (meth)acrylate, n-propyl (meth)acrylate, isopropyl (meth)acrylate, n-butyl (meth)acrylate, isobutyl (meth)acrylate, t-butyl (meth)acrylate, hexyl (meth)acrylate, 2-ethylhexyl (meth)acrylate, octyl (meth)acrylate, isooctyl (meth)acrylate, nonyl (meth)acrylate, isononyl (meth)acrylate, decyl (meth)acrylate, isodecyl (meth)acrylate, lauryl (meth)acrylate, hexadecyl (meth)acrylate, stearyl (meth)acrylate, isostearyl (meth)acrylate, phenyl (meth)acrylate, benzyl (meth)acrylate, cyclohexyl (meth)acrylate, tetrahydrofurfuryl (meth)acrylate, isobornyl (meth)acrylate, and terpene acrylate and a derivative thereof;

hydroxyl group-containing (meth)acrylic acid esters such as 2-hydroxyethyl (meth)acrylate, 2-hydroxypropyl (meth)acrylate, 2-hydroxybutyl (meth)acrylate, 3-hydroxybutyl (meth)acrylate, and 4-hydroxybutyl (meth)acrylate;

carboxyl group-containing vinyl-based monomers such as (meth)acrylic acid;

epoxy group-containing vinyl-based monomers such as glycidyl (meth)acrylate and glycidyl α-ethyl acrylate;

amino group-containing (meth)acrylic acid ester-based vinyl monomers such as dimethylaminoethyl (meth)acrylate and diethylaminoethyl (meth)acrylate;

vinyl-based monomers containing an amide group, such as (meth)acrylamide, N-methyl (meth)acryl amide, N,N'-dimethyl (meth)acrylamide, N-isopropyl acrylamide, N-(hydroxymethyl) acrylamide;

polyfunctional vinyl-based monomers such as ethylene glycol di(meth)acrylate, 1,3-butylene glycol di(meth)acrylate, 1,4-butanediol di(meth)acrylate, 1,6-hexanediol di(meth)acrylate, diethylene glycol di(meth)acrylate, triethylene glycol di(meth)acrylate, tetraethylene glycol di(meth)acrylate, pentaerythritol tetra(meth)acrylate, allyl (meth)acrylate, and N,N'-methylene bis(meth)acrylamide;

heterocyclic ring-based monomers such as (meth)acryloyl morpholine, vinyl pyrrolidone, vinyl pyridine, and vinyl carbazole;

silane coupling agent-containing monomers such as 3-(meth)acryloxypropyl trimethoxysilane, 3-(meth)acryloxypropylmethyl diethoxysilane, 3-(meth)acryloxypropyl triethoxysilane, and 3-acryloxypropyl trimethoxysilane, organosilyl group-containing monomers other than the silane coupling agent-containing monomers, such as trimethylsilyl (meth)acrylate, triethylsilyl (meth)acrylate, tri-n-propylsilyl (meth)acrylate, tri-n-butylsilyl (meth)acrylate;

fluorine-containing monomers (however, the halogenated olefins are excluded) such as 2,2,2-trifluoroethyl (meth)acrylate and 2,2,3,3-tetrafluoropropyl (meth)acrylate, or monomers having an acetal structure such as 1-butoxyethyl (meth)acrylate and 1-(2-ethylhexyloxy)ethyl (meth)acrylate.

The total mass of the constitutional unit (b) is preferably more than a total mass of the constitutional unit (a) in all constitutional units.

The proportion of the constitutional unit (b) is preferably more than 50% by mass and 95% by mass or less, more preferably more than 50% by mass and 80% by mass or less, and still more preferably more than 50% by mass and 75% by mass or less, with respect to the total mass of the constitutional unit (a) and the constitutional unit (b) which are present in the copolymer. In a case where the proportion of the constitutional unit (b) is equal to or more than the lower limit value, the protein adsorption suppressing effect is excellent, and in a case where the proportion of the constitutional unit (b) is equal to or less than the upper limit value, the moldability is excellent.

In a case where the copolymer contains the constitutional unit (c), the total mass of the constitutional unit (c) is preferably 0.5% to 33% by mass, more preferably 0.5% to 25% by mass, and still more preferably, 0.5% to 20% by mass, with respect to the total mass of all the constitutional units.

In a case where the content of the constitutional unit (c) is equal to or more than the lower limit value of the above range, the coating film property is excellent, and in a case where the content of the constitutional unit (c) is equal to or less than the upper limit value, the moldability is excellent.

The weight-average molecular weight of the copolymer is preferably 75,000 or more, more preferably 75,000 or more and 1,000,000 or less, and still more preferably 80,000 or more and 500,000 or less. In a case where the weight-average molecular weight of the copolymer is equal to or more than the lower limit value of the above range, the coating film property is excellent, and in a case where the content of the constitutional unit (c) is equal to or less than the upper limit value, the moldability is excellent.

The weight-average molecular weight of the copolymer is measured by gel permeation chromatography (GPC) using polystyrene as a reference resin.

<Method for Producing Copolymer>

The method for producing a copolymer of the present embodiment is a method for performing bulk polymerization, suspension polymerization, or solution polymerization of a monomer mixture (I-1) containing a macromonomer (d') and the monomer (b').

The above producing method is preferably a method for performing suspension polymerization of the raw material composition (I) containing 0.001 to 5 parts by mass of a non-metal chain transfer agent with respect to 100 parts by mass of the monomer mixture (1-1).

The raw material composition (I) preferably contains a dispersing agent.

In a case where the suspension polymerization is performed, a copolymer which has excellent moldability and is easily processed can be obtained. In a case where the solution polymerization is performed, a copolymer having a narrow molecular weight distribution can be obtained. For example, a bead-shaped copolymer may be recovered from a suspension obtained by suspension polymerization and used for producing a molded body, or the bead-shaped copolymer may be molded into a pellet shape and used in the production of a molded body. For example, the polymer solution obtained by solution polymerization is dropwise added into a poor solvent to perform reprecipitation, or the solvent or the like is removed by a method such as degassing extrusion to recover a powdery copolymer, which may be used for the production of a molded body. Alternatively, the powdery copolymer may be molded into a pellet shape and used in the production of a molded body.

Examples of the preferred method for performing suspension polymerization of the copolymer include a method (A), a method (B), and a method (C).

In the method (A), the macromonomer (d') is dissolved in the monomer (b') to prepare the monomer mixture (I-1), and then a radical polymerization initiator and, as necessary, a non-metal chain transfer agent are added to the monomer mixture (1-1) to prepare the raw material composition (I). Then, the raw material composition (I) is dispersed in an aqueous solution to which, as necessary, a dispersing agent is added to prepare a syrup dispersion liquid of the raw material composition (I), and the obtained syrup dispersion liquid of the raw material composition (I) is subjected to the suspension polymerization.

In the method (B), first, the monomer (b') is added to an aqueous suspension obtained by dispersing, in water, the macromonomer (d') and a dispersing agent which is added as necessary, and a syrup dispersion liquid of the monomer mixture (I-1) is prepared. A radical polymerization initiator and, as necessary, a non-metal chain transfer agent are added to this syrup dispersion liquid of the monomer mixture (1-1) to prepare the syrup dispersion liquid of the raw material composition (I). Then, the syrup dispersion liquid of the raw material composition (1) is subjected to suspension polymerization.

In the method (C), the macromonomer (d') is dissolved in the monomer (b') to prepare the monomer mixture (I-1), and then a radical polymerization initiator and, as necessary, a non-metal chain transfer agent are added to the monomer mixture (1-1) to prepare the raw material composition (I). Then, the raw material composition (I) is dispersed in water to prepare a syrup dispersion liquid of the raw material composition (1). Next, a dispersing agent is added immediately before polymerization, and then the syrup dispersion liquid of the raw material composition (I) is subjected to suspension polymerization.

Here, the "aqueous suspension" means a state in which a monomer or a syrup is dispersed in water.

In the method (A), particles having a uniform composition can be easily obtained by producing a syrup in which macromonomer particles are completely dissolved in the monomer (b'). As a result, in the case of a copolymer obtained by the method (A), the mechanical strength of the molded body obtained from the copolymer is excellent.

In the method (B), the recovery process of the macromonomer (d') can be omitted, and thus the producing process can be shortened. That is, in the method (B), since a suspension obtained by synthesizing a macromonomer (d') by the suspension polymerization method is used as the aqueous suspension and it is possible to perform copolymerization by adding the monomer (b') to this suspension, the process of recovering the macromonomer (d') can be omitted. As the method for synthesizing the macromonomer (d') by the suspension polymerization method, a conventionally known method can be used.

On the other hand, in the method (A), the macromonomer (d') synthesized by the suspension polymerization method is recovered as particles and used.

In the method (C), it is possible to stabilize the monomer dispersion state in the system, and thus particles having a uniform composition are easily obtained as compared with the method (A).

In any method of the method (A), the method (B), or the method (C), it is preferable to raise the temperature in a case of dissolving the macromonomer (d') in the monomer (b').

The heating temperature at the time of dissolving the macromonomer (d') in the monomer (b') is preferably 30° C. to 90° C. In a case where the heating temperature is 30° C. or higher, the solubility of the macromonomer (d') in the monomer (b') tends to be good, and in a case where the heating temperature is 90° C. or lower, the volatilization of the monomer mixture (I-1) tends to be capable of being suppressed. The lower limit of the heating temperature is more preferably 35° C. or higher. Further, the upper limit of the heating temperature is more preferably 75° C. or lower. That is, in a case where the macromonomer (d') is dissolved in the monomer (b'), the monomer mixture (I-1) is preferably heated to 30° C. to 90° C., and more preferably heated to 35° C. to 75° C.

In a case where a radical polymerization initiator is used when polymerizing the monomer mixture (I-1) containing the macromonomer (d'), the timing of adding the radical polymerization initiator is preferably after dissolving the macromonomer (d') in the monomer (b'). That is, it is preferable that the macromonomer (d') is dissolved in the monomer (b') to prepare the monomer mixture (I-1), and then a radical polymerization initiator is added to the monomer mixture (1-1).

The temperature of the monomer mixture (I-1) at the time of adding the radical polymerization initiator is preferably equal to or higher than 0° C. and equal to or lower than the temperature obtained by subtracting 15° C. from the 10-hour half-life temperature of the radical polymerization initiator to be used. In a case where the temperature at the time of adding the radical polymerization initiator is 0° C. or higher, the solubility of the radical polymerization initiator in the monomer (b') tends to be good. Further, in a case where the temperature at the time of adding the radical polymerization initiator is equal to or lower than the temperature obtained by subtracting 15° C. from the 10-hour half-life temperature of the radical polymerization initiator, stable polymerization tends to be capable of being performed.

Examples of the radical polymerization initiator include an organic peroxide and an azo compound.

Specific examples of the organic peroxide include 2,4-dichlorobenzoyl peroxide, 1-butyl peroxypivalate, o-methylbenzoyl peroxide, bis-3,5,5-trimethylhexanoyl peroxide, octanoyl peroxide, t-butylperoxy-2-ethyl hexanoate, cyclohexanone peroxide, benzoyl peroxide, methyl ethyl ketone peroxide, dicumyl peroxide, lauroyl peroxide, diisopropyl benzene hydroperoxide, t-butyl hydroperoxide, and di-t-butyl peroxide.

Specific examples of the azo compound include 2,2'-azobisisobutyronitrile, 2,2'-azobis(2-methylbutyronitrile), 2,2'-azobis(2,4-dimethylvaleronitrile), and 2,2'-azobis(2,4-dimethyl-4-methoxyvaleronitrile).

Among the above radical polymerization initiators, benzoyl peroxide, 2,2'-azobisisobutyronitrile, 2,2'-azobis(2-methylbutyronitrile), 2,2'-azobis(2,4-dimethylvaleronitrile), or 2,2'-azobis(2,4-dimethyl-4-methoxyvaleronitrile) is preferable in terms of the easiness of availability.

The radical polymerization initiator can be used alone or in a combination of two or more thereof.

The amount of the radical polymerization initiator to be added is preferably 0.0001 parts by mass or more and 10 parts by mass or less and more preferably 0.0005 parts by mass or more and 5 parts by mass or less, with respect to 100 parts by mass of the total amount of the macromonomer (d') and the monomer (b') in terms of controlling the heat generation of polymerization.

In the method (A) or the method (B) which are described above, the polymerization temperature at the time of performing suspension polymerization of the raw material composition (I) is not particularly limited, and it is generally preferably 50° C. to 120° C. and more preferably 70° C. to 100° C.

The polymerization time is preferably 1 to 6 hours and more preferably 1.5 to 4 hours.

The stirring condition is preferably 100 to 800 rpm and more preferably 150 to 600 rpm.

Examples of the dispersing agent to be used for suspension polymerization include an alkali metal salt of a poly (meth)acrylic acid, a copolymer of an alkali metal salt of (meth)acrylic acid and a (meth)acrylic acid ester, a copolymer of an alkali metal salt of a sulfoalkyl (meth)acrylate and a (meth)acrylic acid ester, an alkali metal salt of polystyrene sulfonic acid, a copolymer of an alkali metal salt of styrene sulfonic acid and a (meth)acrylic acid ester, a copolymer of an alkali metal salt of (meth)acrylic acid, an alkali metal salt of sulfoalkyl (meth)acrylate, an alkali metal salt of styrene sulfonic acid, and a (meth)acrylic acid ester, a copolymer of an alkali metal salt of (meth)acrylic acid, and an alkali metal salt of sulfoalkyl (meth)acrylate, and a (meth)acrylic acid ester, a copolymer of an alkali metal salt of (meth)acrylic acid, an alkali metal salt of styrene sulfonic acid, and (meth)acrylic acid ester, and a copolymer of an alkali metal salt of sulfoalkyl (meth)acrylate, an alkali metal salt of styrene sulfonic acid, and a (meth)acrylic acid ester, a polyvinyl alcohol having a saponification degree of 70% to 100%; methyl cellulose; starch; and hydroxyapatite. These may be used alone or in a combination of two or more thereof. Among these, a copolymer of an alkali metal salt of sulfoalkyl (meth)acrylate and a (meth)acrylic acid ester, where the copolymer has good dispersion stability at the time of performing suspension polymerization, is preferable.

The content of the dispersing agent is preferably 0.005% to 5% by mass and more preferably 0.01% to 1% by mass, with respect to the total mass of the aqueous suspension. In a case where the content of the dispersing agent in the aqueous suspension is 0.005% by mass or more, the dispersion stability of the suspension polymerization solution is good, and the washability, the dehydration property, the drying property, and the fluidity of the polymer to be obtained tend to be good. Further, in a case where the content of the dispersing agent is 5% by mass or less, foaming during polymerization tends to hardly occur, and thus the polymerization stability tends to be good.

An electrolyte such as sodium carbonate, sodium sulfate, or manganese sulfate may be added to the aqueous suspension for the purpose of improving the dispersion stability of the aqueous suspension. In this case, the proportion of this additive in the case of the method (A) is preferably 0.01% to 0.5% by mass with respect to the total mass of the aqueous suspension. Further, in the case of the method (B), the preferred proportion of the electrolyte in the aqueous suspension is preferably 0.01% to 10% by mass.

It is preferable to polymerize the monomer mixture (1-1) and the raw material composition (I) which contains a non-metal chain transfer agent described later to obtain a copolymer.

<Non-Metal Chain Transfer Agent>

The non-metal chain transfer agent is added to the monomer mixture (I-1) at the time of obtaining a polymer and is particularly preferably added at the time of obtaining a polymer by the suspension polymerization method.

In a case where the non-metal chain transfer agent is used as the chain transfer agent at the time of producing a polymer, the unreacted macromonomer contained in the polymer can be reduced.

Examples of the non-metal chain transfer agents include sulfur-containing chain transfer agents such as t-dodecyl mercaptan and n-octyl mercaptan, an α-methyl styrene dimer, carbon tetrachloride, and a terpenoid; however, from the viewpoint of easiness of availability and having a high chain transfer ability, a sulfur-containing chain transfer agent is preferable.

The content of the non-metal chain transfer agent is preferably 0.01 to 0.5 parts by mass with respect to 100 parts by mass of the monomer mixture (1-1).

In a case where the content of the non-metal chain transfer agent is equal to or more than the lower limit value of the above range, the addition effect is sufficiently obtained, and in a case where the content of the non-metal chain transfer agent is equal to or less than the upper limit value, the mechanical strength after curing is excellent.

The content of the non-metal chain transfer agent is more preferably 0.03 to 0.3 parts by mass and particularly preferably 0.05 to 0.2 parts by mass.

The copolymer of the present embodiment has a protein adsorption suppressing function, and a fibrinogen adsorption amount of 45 nanograms (ng) or less per 1 $cm^2$ at a fibrinogen concentration of 34 ppm (mass basis) can be achieved in the following protein adsorption test (1). The fibrinogen adsorption amount is preferably 30 ng or less and more preferably 20 ng or less.

Further, in the copolymer of the present invention, an albumin adsorption amount of 320 nanograms (ng) or less per 1 $cm^2$ at an albumin concentration of 2,000 ppm (mass basis) can be achieved. The albumin adsorption amount is preferably 300 ng or less.

[Protein Adsorption Test (1)]

A copolymer to be tested is dissolved in methyl cellosolve, which is a solvent, to prepare a copolymer solution having a copolymer concentration of 0.1% to 0.5% by mass. A sensor chip of a quartz crystal microbalance device is spin-coated with the copolymer solution so that the coating amount of the copolymer per unit area is 20.7 $ng/mm^2$ to 62 $ng/mm^2$ and dried at 80° C. for 15 minutes, whereby the copolymer is immobilized on the sensor chip.

The surface of the sensor chip is washed in advance so that reproducibility can be obtained. For example, a method of performing washing by irradiation with excimer light having a wavelength of 172 nm or a method of dropwise adding a piranha solution onto the surface of the sensor chip, allowing it to stand for 5 to 10 minutes, and then washing with pure water can be used.

Fibrinogen (derived from human plasma) is dissolved in the phosphate buffer (water: 99.0435% by weight, sodium chloride: 0.9% by weight, disodium hydrogen phosphate: 0.0421% by weight, potassium dihydrogen phosphate: 0.0144% by weight, pH: 7.1 to 7.3) so that the concentration thereof is to be a predetermined concentration, thereby obtaining a test solution. The fibrinogen concentration of the test solution is set to 1,000 (unit: mass ppm).

After stabilizing the surface of the sensor chip by immersing it in the phosphate buffer for 12 hours or more, and in the specified amount of the phosphate buffer, the sensor is set again in the quartz crystal microbalance device, and the transmission frequency measurement is started. After stabilizing the transmission frequency for about 30 minutes to 1 hour, the test solution is dropwise added every 15 minutes. The amount to be dropwise added at one time is 0.5 to 1.0 µL. From the measurement data of the transmission frequency, the amount of fibrinogen adsorbed to the sensor is calculated. The measurement data can be analyzed using analysis software. From the graph showing the correlation between the fibrinogen concentration in the system into which the test solution has been dropwise added and the amount adsorbed to the sensor, the fibrinogen adsorption amount per sensor area (4.8 $mm^2$) at a fibrinogen concentration of 34 ppm (mass basis) is determined.

Regarding albumin (BSA, derived from bovine), the measurement can be also performed in the same manner. At that time, the albumin concentration of the test solution is set to 10,000 and 30,000 (unit: mass ppm). From the graph showing the correlation between the albumin concentration and the amount adsorbed to the sensor, the albumin adsorption amount per sensor area (4.8 $mm^2$) at an albumin concentration of 2,000 ppm (mass basis) is determined.

<Use>

As will be described in Practical Examples described later, the copolymer of the present embodiment has excellent moldability, from which a molded body having a protein adsorption suppressing effect is obtained, and thus is suitable for producing an article that comes in contact with a protein. The copolymer of the present embodiment is particularly suitable for producing an article that comes in contact with a plasma protein.

The copolymer of the present embodiment is suitable as a resin modifier. In a case where the resin modifier made of the copolymer is added to the resin composition, the protein adsorption suppressing effect of the resin composition can be improved.

The copolymer of the present embodiment is suitable as a molding material. In a case where a molding material containing the copolymer is molded, an article (a molded body) having a protein adsorption suppressing effect can be obtained.

<Molding Material>

The molding material may contain, as necessary, another polymer in addition to the copolymer. Further, another component may be contained as necessary.

Examples of the other polymer include (meth)acrylic resins such as PMMA, polyolefin, polystyrene, polyamide, polyurethane, an unsaturated polyester, saturated polyesters such as polyethylene terephthalate and polybutylene terephthalate, polycarbonate, polyvinyl chloride, a silicone resin, an epoxy resin, polyether ether ketone, and polyvinylidene fluoride. The other polymer is preferably a thermoplastic resin, and among them, a (meth)acrylic resin or an olefin resin is preferable.

Examples of the other component include a mold release agent, an antioxidant, a heat stabilizer, an impact resistance improver, a flexibility enhancer, a weather resistance improver, a colorant, an inorganic pigment, an organic pigment, carbon black, ferrite, a conductivity imparting agent, an ultraviolet absorber, an infrared absorber, a lubricant, an inorganic filler, a strengthening agent, a plasticizer, a reverse plasticizer, a neutralizer, a cross-linking agent, a flame retardant, a preservative, an insect repellent, a fragrance, a radical scavenger, a sound absorbing material, and a core shell rubber.

Examples of the method of mixing the copolymer, the other polymer, and the other component that is blended as necessary include a physical method of mixing with as a Henschel mixer, a blender, or the like, and a method of performing melt-kneading with a mixer such as a Brabender, a kneader, or an extruder.

The shape of the molding material is not particularly limited, but in a case where it is assumed that the molding material is used for melt-molding into a molded body, it is preferable that the copolymer, the other polymer, and the other component that is blended as necessary are melt-kneaded in advance to be processed into a pellet shape or a bead shape.

The content of the copolymer with respect to the total mass of the molding material is preferably 1% by mass or more, more preferably 5% by mass or more, and still more preferably 10% by mass or more. The content of the copolymer may be 100% by mass. In a case where the content of the copolymer is equal to or more than the above lower limit value, the protein adsorption suppressing ability is excellent.

The other polymer is preferably 0% to 95% by mass and more preferably 20% to 80% by mass, with respect to the total mass of the molding material.

The molding material containing the copolymer of the present embodiment has a protein adsorption suppressing function, and an albumin adsorption amount of 1.5 micrograms (µg) or less per 1 cm$^2$ can be achieved in the following protein adsorption test (2). The albumin adsorption amount is preferably 1.25 µg or less and more preferably 1.10 µs or less.

[Protein Adsorption Test (2): µBCA Method]

A molding material to be tested is immersed in an albumin solution of 1 mg/mL obtained by dissolving the albumin in phosphate buffered saline (PBS), at 37° C. for 2 hours. After inserting for 2 hours, the molding material is washed with PBS, immersed in 6 mL of an aqueous sodium dodecyl sulfate solution, and then subjected to ultrasonic washing for 5 minutes. 150 µL of the ultrasonically washed solution is put into a 96-well plate, and 150 µL of a commercially available BCA kit protein quantification reagent is put into the portion where the ultrasonically washed solution has been put, followed by being kept at 37° C. for 2 hours. After holding for 2 hours, the absorbance at 562 nm is measured with a plate reader, and the albumin adsorption amount is calculated by applying the measured value to a calibration curve obtained from albumin solutions having a known concentration.

<Molded Article>

Examples of the shape of the article (the molded body) include a sheet shape and a three-dimensional shape.

The method for molding the molding material to produce an article (a molded body) is preferably a melt molding method, and examples thereof include an injection molding method, a compression molding method, a hollow molding method, an extrusion molding method, a rotary molding method, a casting method, and a solvent casting method. Among these, injection molding or extrusion molding is preferable.

The article (the molded body) is preferably an article that comes in contact with a protein and is preferably used as an inner layer of a multilayer film, which comes in contact with a plasma protein, an antibody drug, or a biopharmacy drug.

Examples of the article that comes in contact with a plasma protein include medical instrument such as a contact lens, a cannula, a catheter, an injection tube, an infusion route, an infusion bag, an infusion solution bag, a blood bag, a stent, and an endoscope; biochemical instruments such as a pipette tip, a petri dish, a cell, a microplate, a storage bag, a plate, a reagent storage container, a tube, and a flask; and cell therapy apparatuses such as a mixer, a bioreactor, and a jar fermenter.

In addition, examples of the article that comes in contact with a protein other than the plasma protein include a petri dish for cell culture, a cell for cell culture, a microplate for cell culture, a bag for cell culture, a plate for cell culture, a tube for cell culture, a flask for cell culture, a petri dish for biopharmacy, a cell for biopharmacy, a microplate for biopharmacy, a plate for biopharmacy, a tube for biopharmacy, a bag for biopharmacy, a container for biopharmacy, a syringe for biopharmacy, a flask for biopharmacy, a petri dish for antibody drug, a cell for antibody drug, a microplate for antibody drug, a plate for antibody drug, a tube for antibody drug, a bag for antibody drug, a container for antibody drug, and a syringe for antibody drug, a flask for antibody drug, a blood (whole blood, plasma, platelet, red blood cell) bag, a vial for blood product, and a bag for blood product.

<Coating Film>

The copolymer of the present embodiment can be used by being dissolved in a solvent. As will be described in Practical Examples described later, the coating film formed by using the copolymer-containing composition containing the copolymer and the solvent contains the copolymer and has a protein adsorption suppressing effect. The copolymer contained in the copolymer-containing composition may be one kind or two or more kinds.

It is preferable to form a coating film using the copolymer-containing composition at least on the surface of the article that comes in contact with a protein, where the surface comes in contact with a protein. It is particularly preferable to form a coating film using the copolymer-containing composition at least on the surface of the article that comes in contact with a plasma protein, where the surface comes in contact with a plasma protein.

The solvent in the copolymer-containing composition is not particularly limited as long as it can dissolve the copolymer of the present embodiment. Examples thereof include monohydric alcohols such as methyl alcohol, ethyl alcohol, and isopropyl alcohol; polyhydric alcohols such as ethylene glycol and 1,2-propylene glycol; ketones such as acetone, methyl ethyl ketone, acetylacetone, butyl acetate; ethers such as methyl ethyl ether and dioxane; glycol ethers such as ethylene glycol monomethyl ether, ethylene glycol monoethyl ether, propylene glycol monomethyl ether, propylene glycol monoethyl ether, propylene glycol mono n-propyl ether, ethylene glycol dimethyl ether, diethylene glycol monomethyl ether, diethylene glycol dimethyl ether, and dipropylene glycol monopropyl ether; glycol acetates such as ethylene glycol monoacetate, ethylene glycol diacetate, and ethylene glycol monomethyl ether acetate; aliphatic hydrocarbons such as n-pentane and n-hexane; aromatic hydrocarbons such as toluene, xylene, and solvent naphtha.

Any one of these can be used alone or in a combination of two or more thereof.

The content of the solvent with respect to the copolymer-containing composition is preferably 15% to 99% by mass, more preferably 20% to 95% by mass, and particularly preferably 25% to 90% by mass. In a case where the content of the solvent is equal to or more than the above lower limit value, the coatability is excellent.

The copolymer-containing composition may further contain another component other than the copolymer.

The content of the copolymer with respect to the copolymer-containing composition is preferably 1% to 85% by mass, more preferably 5% to 80% by mass, still more preferably 10% to 75% by mass, and particularly preferably 15% to 70% by mass. In a case where the content of the copolymer is equal to or more than the lower limit value, the protein adsorption suppressing effect of the coating film is excellent.

The content of the copolymer with respect to the total solid content of the copolymer-containing composition is preferably 10% by mass or more and more preferably 30% by mass or more. The content of the copolymer may be 100% by mass.

The method for forming the coating film using the copolymer-containing composition is not particularly limited. For example, the coating film can be formed on the base material by a coating method such as a dip, a spraying method, or a spin coating method.

The material of the base material is not particularly limited, but a material of which the surface can be coated, such as polystyrene, polypropylene, polyethylene, polyurethane, vinyl chloride, nylon, a silicone resin, glass, and a metal such as stainless steel is used.

Examples of the article having the coating film on the surface thereof, where the surface comes in contact with a plasma protein, include medical instruments such as a scalpel, a forceps, a contact lens, a cannula, a catheter, an injection tube, an injection needle, an infusion route, an infusion needle, an infusion bag, a blood bag, gauze, a stent, and an endoscope; biochemical instruments such as a pipette tip, a petri dish, a cell, a microplate, a storage bag, a plate, a reagent storage container, and a tube; and cell therapy apparatuses such as a mixer, a bioreactor, and a jar fermenter.

In addition, examples of the article having the coating film on the surface thereof, where the surface comes in contact with a protein other than the plasma protein include a petri dish for cell culture, a cell for cell culture, a microplate for cell culture, a bag for cell culture, a plate for cell culture, a tube for cell culture, a flask for cell culture, a petri dish for biopharmacy, a cell for biopharmacy, a microplate for biopharmacy, a plate for biopharmacy, a tube for biopharmacy, a bag for biopharmacy, a container for biopharmacy, a syringe for biopharmacy, a flask for biopharmacy, a petri dish for antibody drug, a cell for antibody drug, a microplate for antibody drug, a plate for antibody drug, a tube for antibody drug, a bag for antibody drug, a container for antibody drug, and a syringe for antibody drug, a flask for antibody drug, blood (whole blood, plasma, platelet, red blood cell) bag, a vial for blood product, and a bag for blood product.

EXAMPLES

Hereinafter, the present invention will be described in more detail according to Practical Examples and Comparative Examples, but the present invention is not limited to these examples. The "parts" in Practical Examples represents "parts by mass".

<Measurement Method and Evaluation Method>

(Weight-Average Molecular Weight (Mw) and Number-Average Molecular Weight (Mn))

The weight-average molecular weight and the number-average molecular weight were measured using gel permeation chromatography (CPC) (manufactured by Tosoh Corporation, HLC-8220). As the column, TSKgel α-M (manufactured by Tosoh Corporation, 7.8 mm×30 cm) and TSKguardcolumn α (manufactured by Tosoh Corporation, 6.0 mm×4 cm) were used. A calibration curve was prepared using F288/F1/28/F80/F40/F20/F2/A1000 (manufactured by Tosoh Corporation, standard polystyrene) and a styrene monomer.

(Evaluation of Moldability)

A copolymer or a polymer of each example was molded by a press molding machine manufactured by SHOJI Co., Ltd. The molding conditions were kept at 200° C. and 18 MPa for 5 minutes to prepare a test plate having a thickness of 2 mm.

The appearance and releasability of the test piece obtained by press molding were observed, and the moldability was evaluated according to the following criteria.

A: No molding defects are observed, and releasability is good.
B: No molding defects are observed, and releasability is poor.
C: Molding is possible, but molding defects occur.
D: Molding is difficult.

(Indentation Elasticity Modulus)

The indentation elasticity modulus of the test plate produced in the above-described evaluation of moldability was measured using a Vickers indenter with a micro-hardness tester (HM-2000, manufactured by Fischer Instruments K.K.) under the measurement conditions of a load of 7 mN/100s, a creep of 60 s, and R=0.4 mN/100 s.

(Protein Adsorption Test 1)

Bovine serum albumin (abbreviation: BSA, FUJIFILM Wako Pure Chemical Corporation) was used as the protein for analyzing the adsorption amount, and the correlation between the BSA concentration and the adsorption amount per sensor area (4.8 mm$^2$) was obtained by the protein adsorption test (1) described above.

As a measuring device, a quartz crystal microbalance (QCM) device (AFFNIX Q8, manufactured by ULVAC, Inc.) was used.

For the washing treatment of the sensor chip, an electrodeless excimer 172 nm irradiation apparatus (model number: MDIRH-M-1-330, manufactured by M.D.COM. Inc.) was used. The surface of the sensor chip was set to be within the treatment range, subjected to the treatment 20 times at 5 mm/sec in the automatic transfer mode, and the surface of the sensor chip was washed and hydrophilized.

An analysis software (AQUA, manufactured by ULVAC, Inc.) was used for the analysis of the measurement data.

(Protein Adsorption Test 2)

Measurement and analysis were carried out in the same manner as in the protein adsorption test 1, except that the protein for which the adsorption amount was analyzed was fibrinogen (derived from human plasma, FUJIFILM Wako Pure Chemical Corporation).

(Protein Adsorption Test 3)

The amount of BSA adsorbed to the molding material was evaluated by the protein adsorption test (2) (μBCA method).

(Protein Adsorption Test 4)

Measurement and evaluation were carried out in the same manner as in the protein adsorption test 3, except that the adsorption protein was fibrinogen (derived from human plasma, FUJIFILM Wako Pure Chemical Corporation).
(Protein Adsorption Test 5)

Measurement and evaluation were carried out in the same manner as in the protein adsorption test 3, except that the adsorption protein was γ globulin (derived from human plasma, FUJIFILM Wako Pure Chemical Corporation).

Production Example 1

In a polymerization apparatus equipped with a stirrer, a cooling tube, and a thermometer, 900 parts of deionized water, 60 parts of sodium 2-sulfoethyl methacrylate, 10 parts of potassium methacrylate, and 12 parts of methyl methacrylate (MMA) were added and stirred, and the temperature inside of the polymerization apparatus was raised to 50° C. while replacing the atmosphere inside of the polymerization apparatus with nitrogen. Then, 0.08 parts of 2,2'-azobis(2-methylpropionamidine)dihydrochloride as a polymerization initiator was added therein, and the temperature was further raised to 60° C. After the temperature was raised, MMA was continuously added dropwise at a rate of 0.24 parts/minute for 75 minutes using a dropping pump. The reaction solution was kept at 60° C. for 6 hours and then cooled to room temperature to obtain a dispersing agent 1 having a solid content of 10% by mass as a transparent aqueous solution.

Next, in a polymerization apparatus equipped with a stirrer, a cooling tube, and a thermometer, 145 parts of deionized water, 0.1 parts of sodium sulfate, and 0.25 parts of the dispersing agent 1 (solid content: 10% by mass) were added and stirred to obtain a homogeneous aqueous solution. Next, 100 parts of MMA, 0.0010 parts of bis[(difluoroboryl)diphenylglioxymate] cobalt (II) as a chain transfer agent, and 0.1 parts of "PEROCTA O" (registered trade mark) (1,1,3,3-tetramethylbutylperoxy 2-ethyl hexanoate, manufactured by NOF Corporation) as a polymerization initiator were added thereto to prepare an aqueous suspension.

Next, the inside of the polymerization apparatus was replaced with nitrogen, the temperature was raised to 80° C., the reaction was performed for 4 hours, and then, in order to further increase the polymerization rate, the temperature was raised to 90° C. and held for 2 hours. Then, the reaction solution was cooled to 40° C. to obtain an aqueous suspension containing a macromonomer. The aqueous suspension was filtered, the filtrate was washed with deionized water, dehydrated, and dried at 40° C. for 16 hours to obtain a macromonomer (MM1). The number-average molecular weight of this macromonomer (MM1) was 15,000, and the molecular weight distribution (Mw/Mn) was 2.4.

Production Example 2

The same procedure was performed as in Production Example 1, except that 100 parts of MMA, 0.0009 parts of bis[(difluoroboryl)diphenylglioxymate] cobalt (II) as a chain transfer agent, and 0.12 parts of "PEROCTA O" (registered trade mark) (1,1,3,3-tetramethylbutylperoxy 2-ethyl hexanoate, manufactured by NOF Corporation) as a polymerization initiator were added. The number-average molecular weight of the obtained macromonomer (MM2) was 21,000, and the molecular weight distribution (Mw/Mn) was 2.1.

Production Example 3

The same procedure was performed as in Production Example 1, except that 95 parts of MMA, 5 parts of MA, 0.0016 parts of bis[(difluoroboryl)diphenylglioxymate] cobalt (II) as a chain transfer agent, and 0.12 parts of "PEROCTA O" (registered trade mark) (1,1,3,3-tetramethylbutylperoxy 2-ethyl hexanoate, manufactured by NOF Corporation) as a polymerization initiator were added. The number-average molecular weight of the obtained macromonomer (MM3) was 15,000, and the molecular weight distribution (Mw/Mn) was 2.3.

Example 1 below is Practical Example, and Examples 2 to 4 below are Comparative Examples.

In Table 1, St represents styrene, MMA represents methyl methacrylate, MEA represents methoxyethyl acrylate, and n-OM represents n-octyl mercaptan.

Example 1

145 parts of deionized water, 0.3 parts of sodium sulfate, and 0.26 parts of the dispersing agent 1 produced in Production Example 1 were mixed to prepare an aqueous dispersion medium for a suspension.

40 parts of the macromonomer (MM1) produced in Production Example 1, 60 parts of methoxyethyl acrylate (manufactured by Osaka Organic Chemical Industry Ltd.), and 0.2 parts of n-octyl mercaptan (Kanto Chemical Co., Inc., trade name) as a non-metal chain transfer agent were charged in a flask with a cooling tube, and the temperature was raised to 55° C. with stirring to obtain a composition having a syrup state. After cooling the composition to 40° C. or lower, 0.325 parts of AMBN (manufactured by FUJIFILM Wako Pure Chemical Corporation, 2,2'-azobis(2-methylbutyronitrile), trade name) was dissolved in the composition, thereby obtaining a raw material composition.

Next, after adding the above-described aqueous dispersion medium for a suspension to the raw material composition, the stirring rotation speed was increased while replacing the atmosphere in the separable flask with nitrogen by nitrogen bubbling to obtain a syrup dispersion liquid.

The temperature of the syrup dispersion liquid was raised to 75° C. to maintain the outside temperature of the separable flask. After the heat generation peak of polymerization appeared, when the syrup dispersion liquid became 75° C., the temperature of the syrup dispersion liquid was raised to 85° C. and held for 30 minutes to complete the polymerization, whereby a suspension was obtained.

After cooling the suspension to 40° C. or lower, the suspension was filtered through a filter cloth, the filtrate was washed with deionized water, and dried at 70° C. for 12 hours to obtain a copolymer. The molecular weights (Mn and Mw) and physical properties (moldability and indentation elasticity modulus) of the obtained copolymers are shown in Table 1 (the same applies hereinafter).

Table 1 also shows the mass ratio of the constitutional unit (a) to the constitutional unit (b), and the amount of the non-metal chain transfer agent to be added with respect to the total of 100 parts by mass of the constitutional unit (a) and the constitutional unit (b) (the same applies hereinafter).

The obtained copolymer was dissolved in methyl cellosolve, and a protein adsorption test was performed. The results are shown in Table 1 (the same applies hereinafter).

Example 2

100 parts of methoxyethyl acrylate (manufactured by Osaka Organic Chemical Industry Ltd.) and 250 parts of methyl cellosolve (manufactured by Kanto Chemical Co., Inc., special grade reagent) as a solvent were put into a flask with a cooling tube, and the inside of the flask was replaced with nitrogen by nitrogen bubbling. Next, in the state in which the internal temperature of the flask was kept at 70° C. by raising the temperature of the monomer composition in the flask, 0.8 parts of 2,2'-azobisisobutyronitrile (AIBN) (FUJIFILM Wako Pure Chemical Corporation, Wako special grade) as a radical polymerization initiator was added to the monomer composition, held for 4 hours, and then the temperature was raised to 80° C. and held for 1 hour to complete the polymerization. Thereafter, the polymerization reaction product was cooled to room temperature and represipitated with a large amount of diisopropyl ether (Junsei Chemical Co., Ltd.). The polymer precipitated by reprecipitation was recovered and vacuum dried overnight at 50° C. and 50 mmHg (6.67 kPa) or less to obtain a copolymer.

The obtained copolymer was a viscous polymer, had high fluidity, and thus could not be molded.

The obtained copolymer was dissolved in methyl cellosolve, and a protein adsorption test was performed.

Example 3

A polystyrene solution obtained by dissolving a polystyrene powder (standard polystyrene F-4, manufactured by Tosoh Corporation) having a number-average molecular weight of 50,000 and a weight-average molecular weight of 50,500 in xylene (manufactured by FUJIFILM Wako Pure Chemical Corporation) was applied onto the base material by spin coating and then dried to form a coating film. A protein adsorption test was performed on the obtained coating film. Further, the moldability was evaluated by the above method.

Example 4

A polymethyl methacrylate solution obtained by dissolving polymethyl methacrylate (manufactured by Mitsubishi Chemical Corporation, VHK000) having a number-average molecular weight of 54,900 and a weight-average molecular weight of 108,000 in xylene (manufactured by FUJIFILM Wako Pure Chemical Corporation) was applied onto the base material by spin coating and then dried to form a coating film. A protein adsorption test was performed on the obtained coating film. Further, the moldability was evaluated by the above method.

TABLE 1

| | | Example 1 | Example 2 | Example 3 | Example 4 |
|---|---|---|---|---|---|
| Constitutional unit (a) (parts by mass) | MM1 | 40 | — | — | — |
| | St | — | — | 100 | — |
| | MMA | — | — | — | 100 |
| Constitutional unit (b) (parts by mass) | MEA | 60 | 100 | — | — |
| Non-metal chain transfer agent (parts by mass) | n-OM | 0.2 | — | — | — |
| Molecular weight of (co)polymer | Mn | 44,000 | 7,000 | 50,000 | 54,900 |
| | Mw | 362,000 | 21,000 | 50,500 | 108,000 |
| Protein adsorption test 1 (BSA concentration: 2,000 ppm) | BSA adsorption amount (ng/cm$^2$) | 83.63 | 320.38 | 456.80 | 497.55 |
| Protein adsorption test 2 (FB concentration: 34 ppm) | FB adsorption amount (ng/cm$^2$) | 17.5 | 969 | 1380.0 | 1735 |
| Physical property of (co)polymer | Moldability | A | D | A | B |
| | Indentation elasticity modulus (MPa) | 78 | Unmeasurable | 2400 | 3400 |

FIG. 1 is a graph showing the results of the protein adsorption test in Table 1. In FIG. 1, the horizontal axis represents the BSA concentration, and the vertical axis represents the BSA adsorption amount in the copolymer.

As shown in the results of Table 1 and FIG. 1, the copolymer of Example 1 has an excellent protein adsorption suppressing effect as compared with the polymers of Examples 2 to 4.

Further, the molded body of the copolymer of Example 1 has a low indentation elasticity modulus and is excellent in molding processability as compared with the molded bodies of the polymers of Examples 3 and 4.

Examples 5, Example 6, Examples 9 to 23, 24, 26 to 30 are Practical Examples, and Examples 7, 8, 25, and 32 are Comparative Examples.

Example 5

70 parts of polymethyl methacrylate (VHK000) and 30 parts of the copolymer obtained in Example 1 were kneaded with Labo Plastomill at 250° C. and 30 rpm for 5 minutes to prepare a molding material. The obtained molding material was molded by a press molding machine manufactured by SHOJI Co., Ltd. The molding conditions were kept at 200° C. and 18 MPa for 5 minutes to prepare a molded body having a thickness of 2 mm. The obtained molded body was subjected to a protein adsorption test according to the protein adsorption test (2) (μBCA method). The test results are shown in Table 3 (the same applies hereinafter).

Example 6

The same procedure was performed as in Example 5, except that the used amount of the copolymer obtained in Example 1 was changed to 100 parts.

Example 7

The same procedure was performed as in Example 5, except that the used amount of VHK000 was changed to 100 parts.

Example 8

The same procedure was performed as in Example 5, except that the used amount of the olefin resin MC638 (manufactured by Mitsubishi Chemical Corporation, trade name) was changed to 100 parts.

Example 9

51 parts of methoxyethyl acrylate (manufactured by Osaka Organic Chemical Industry Ltd.), 9 parts of 2-hydroxyethyl methacrylate (manufactured by Mitsubishi Chemical Corporation, Acryester (registered trade mark) HO), 40 parts of the macromonomer (MM2) macromonomer produced in Production Example 2, and 150 parts of N,N-dimethylacetamide (manufactured by FUJIFILM Wako Pure Chemical Corporation, special grade reagent) were added in a flask with a cooling tube, and the inside of the flask was replaced with nitrogen by nitrogen bubbling. Next, in the state in which the internal temperature of the flask was kept at 55° C. by raising the temperature of the monomer composition in the flask, 0.1 parts of 2,2'-azobis(2,4'-dimethylvaleronitrile (FUJIFILM Wako Pure Chemical Corporation, trade name: V-65) as a radical polymerization initiator was added to the monomer composition and then held for 4 hours. Next, the temperature was raised to 80° C., 0.15 parts of V-65 was further added, and then the resultant mixture was held for 60 minutes to complete the polymerization. Then, the polymerization reaction product was cooled to room temperature and reprecipitated with a large amount of pure water. The polymer precipitated by reprecipitation was recovered and vacuum dried overnight at 50° C. and 50 mmHg (6.67 kPa) or less to obtain a copolymer. The number-average molecular weight was 66,000 and the weight-average molecular weight was 217,000. The same procedure was performed as in Example 5, except that the used amount of the obtained copolymer was changed to 100 parts by weight.

Example 10

144 parts of deionized water and 0.3 parts of sodium sulfate were mixed to prepare an aqueous dispersion medium for a suspension.

40 parts of the macromonomer (MM3) produced in Production Example 3, 58 parts of methoxyethyl acrylate (manufactured by Osaka Organic Chemical Industry Ltd.), 2 parts of 2-hydroxyethyl methacrylate (manufactured by Mitsubishi Chemical Corporation, Acryester (registered trade mark) HO), and 0.2 parts of n-octyl mercaptan (Kanto Chemical Co., Inc., trade name) as a non-metal chain transfer agent were charged in a flask with a cooling tube, and the temperature was raised to 55° C. with stirring to obtain a composition having a syrup state. After cooling the composition to 40° C. or lower, 0.325 parts of AMBN (manufactured by FUJIFILM Wako Pure Chemical Corporation, 2,2'-azobis(2-methylbutyronitrile), trade name) was dissolved in the composition, thereby obtaining a raw material composition.

Next, after adding the above-described aqueous dispersion medium for a suspension to the raw material composition, the stirring rotation speed was increased while replacing the atmosphere in the separable flask with nitrogen by nitrogen bubbling to obtain a syrup dispersion liquid.

After putting, into a flask, an aqueous dispersion medium obtained by mixing 0.26 parts of the dispersing agent 1 produced in Production Example 1 and 1 part of deionized water, the temperature was raised to 75° C. to maintain the outside temperature of the separable flask. After the heat generation peak of polymerization appeared, when the syrup dispersion liquid became 75° C., the temperature of the syrup dispersion liquid was raised to 85° C. and held for 30 minutes to complete the polymerization, whereby a suspension was obtained.

After cooling the suspension to 40° C. or lower, the suspension was filtered through a filter cloth, the filtrate was washed with deionized water, and dried at 70° C. for 12 hours to obtain a copolymer. The number-average molecular weight was 37,500 and the weight-average molecular weight was 224,000. The same procedure was performed as in Example 5, except that the used amount of the obtained copolymer was changed to 100 parts by weight.

Example 11

The same procedure was performed as in Example 1, except that the macromonomer (MM3) produced in Production Example 3 was used. The number-average molecular weight was 42,700 and the weight-average molecular weight was 295,000. The same procedure was performed as in Example 5, except that the used amount of the obtained copolymer was changed to 100 parts by weight.

The copolymers of Example 1 and Examples 9 to 11 are summarized in Table 2.

Example 12 to Example 18

The same procedure was performed as in Example 5, except that the ratio of the copolymer and the ratio of the thermoplastic resin were changed to the ratios described in Table 4.

Example 19 to Example 25

The same procedure was performed as in Example 5, except that the protein was changed to fibrinogen (FB) and the ratio of the copolymer and the ratio of the thermoplastic resin were changed to the ratios described in Table 5.

Example 26 to Example 32

The same procedure was performed as in Example 5, except that the protein was changed to γ globulin (IgG) and the ratio of the copolymer and the ratio of the thermoplastic resin were changed to the ratios described in Table 6.

TABLE 2

| | | Example 1 | Example 9 | Example 10 | Example 11 |
|---|---|---|---|---|---|
| Constitutional unit (a) (parts by mass) | MM1 | 40 | — | — | — |
| | MM2 | — | 40 | — | — |
| | MM3 | — | — | 40 | 40 |
| | HEMA | — | 9 | 2 | — |
| Constitutional unit (b) (parts by mass) | MEA | 60 | 51 | 58 | 60 |
| Molecular weight of copolymer | Mn | 44,000 | 66,000 | 37,500 | 42,700 |
| | Mw | 362,000 | 217,000 | 224,000 | 295,000 |

*HEMA: 2-hydroxyethyl (meth)acrylate

TABLE 3

|  |  |  | Example 5 | Example 6 | Example 7 | Example 8 | Example 9 | Example 10 | Example 11 |
|---|---|---|---|---|---|---|---|---|---|
| Molding material | Copolymer (% by mass) | Example 1 | 30 | 100 | — | — | — | — | — |
|  |  | Example 9 | — | — | — | — | 100 | — | — |
|  |  | Example 10 | — | — | — | — | — | 100 | — |
|  |  | Example 11 | — | — | — | — | — | — | 100 |
|  | Thermoplastic resin (% by mass) | VHK000 | 70 | — | 100 | — | — | — | — |
|  |  | MC638 | — | — | — | 100 | — | — | — |
| Evaluation | Protein adsorption test 3 (μBCA method) | BSA adsorption amount (μg/cm²) | 1.477 | 0.928 | 2.682 | 2.061 | 1.686 | 1.478 | 0.913 |

TABLE 4

|  |  |  | Example 12 | Example 13 | Example 14 | Example 15 | Example 16 | Example 17 | Example 18 |
|---|---|---|---|---|---|---|---|---|---|
| Molding material | Copolymer (% by mass) | Example 1 | — | — | — | — | — | — | — |
|  |  | Example 9 | — | — | — | — | — | — | — |
|  |  | Example 10 | — | — | — | — | — | — | — |
|  |  | Example 11 | 50 | 10 | 1 | 5 | 10 | 30 | 50 |
|  | Thermoplastic resin (% by mass) | VHK000 | 50 | 90 | — | — | — | — | — |
|  |  | MC638 | — | — | 99 | 95 | 90 | 70 | 50 |
| Evaluation | Protein adsorption test 3 (μBCA method) | BSA adsorption amount (μg/cm²) | 0.987 | 1.775 | 1.854 | 1.375 | 1.188 | 1.029 | 1.012 |

TABLE 5

|  |  |  | Example 19 | Example 20 | Example 21 | Example 22 | Example 23 | Example 24 | Example 25 |
|---|---|---|---|---|---|---|---|---|---|
| Molding material | Copolymer (% by mass) | Example 11 | 100 | -1 | 5 | 10 | 30 | 50 | — |
|  | Thermoplastic resin (% by mass) | MC638 | — | 99 | 95 | 90 | 70 | 50 | 100 |
| Evaluation | Protein adsorption test 4 (μBCA method) | FB adsorption amount (ng/cm²) | 0.835 | 1.626 | 1.533 | 1.337 | 1.241 | 1.113 | 1.810 |

TABLE 6

|  |  |  | Example 26 | Example 27 | Example 28 | Example 29 | Example 30 | Example 31 | Example 32 |
|---|---|---|---|---|---|---|---|---|---|
| Molding material | Copolymer (% by mass) | Example 11 | 100 | 1 | 5 | 10 | 30 | 50 | — |
|  | Thermoplastic resin (% by mass) | MC638 | — | 99 | 95 | 90 | 70 | 50 | 100 |
| Evaluation | Protein adsorption test 5 (μBCA method) | IgG adsorption amount (ng/cm²) | 0.863 | 1.334 | 1.243 | 1.115 | 1.021 | 0.937 | 1.451 |

As shown in the results of Table 3 to Table 6, the molding materials of Examples 5, Example 6, Example 9 to Example 24, and Example 26 to Example 31, which contain the copolymer of the present invention, have an excellent protein adsorption suppressing effect as compared with the molding materials of Example 7, Example 8, Example 25, and Example 32, which do not contain the copolymer of the present invention.

INDUSTRIAL APPLICABILITY

The copolymer of the present invention can impart a protein adsorption suppressor to the molded body.

The copolymer of the present invention can impart a protein adsorption suppressor to the coating film.

The copolymer of the present invention is suitable for producing an article that comes in contact with a protein.

For example, the copolymer of the present invention is suitable for producing an article that comes in contact with a plasma protein, such as medical instruments such as a scalpel, a forceps, a contact lens, a cannula, a catheter, an injection tube, an injection needle, an infusion route, an infusion needle, an infusion bag, a blood bag, gauze, a stent, and an endoscope; and articles that come in contact with a protein, such as a pipette tip, a petri dish, a cell, a microplate, a storage bag, a plate, a reagent storage container, and a tube.

What is claimed is:

1. A molded article that comes in contact with a protein, which is obtained by molding a molding material, containing a copolymer comprising:

a constitutional unit (a) of Formula (1); and a constitutional unit (b) of Formula (2), wherein a total mass of the constitutional unit (b) is more than a total mass of the constitutional unit (a) in all constitutional units,

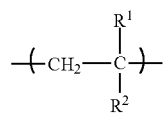
(1)

wherein $R^1$ represents a hydrogen atom or a methyl group, $R^2$ is an $OR^{33}$, a halogen atom, $COR^{34}$, $COOR^{35}$, CN, $CONR^{36}R^{37}$, or $R^{38}$, where $R^{33}$ to $R^{37}$ each independently represent a hydrogen atom, a substituted or unsubstituted alkyl group, a substituted or unsubstituted alicyclic group, a substituted or unsubstituted aryl group, a substituted or unsubstituted heteroaryl group, a substituted or unsubstituted non-aromatic heterocyclic group, a substituted or unsubstituted aralkyl group, a substituted or unsubstituted alkaryl group, or a substituted or unsubstituted organosilyl group, and $R^{38}$ represents a substituted or unsubstituted aryl group or a substituted or unsubstituted heteroaryl group,

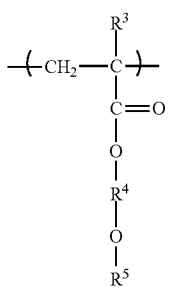
(2)

wherein $R^3$ represents a hydrogen atom or a methyl group, $R^4$ represents an alkylene group having 1 to 4 carbon atoms, and $R^5$ represents a hydrocarbon group having 1 to 6 carbon atoms.

2. The molded article according to claim 1, wherein the constitutional unit (a) is a constitutional unit derived from a (meth)acrylic acid ester.

3. The molded article according to claim 1, wherein the copolymer for suppressing protein adsorption, further comprises:

a constitutional unit (d) derived from a macromonomer containing the constitutional unit (a).

4. The molded article according to claim 3, wherein the macromonomer is of Formula (4),

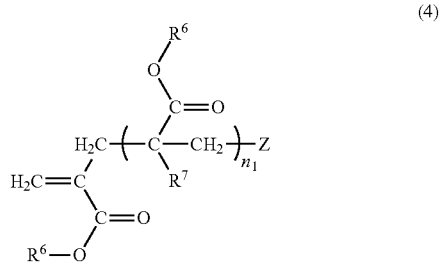
(4)

wherein $R^6$'s each independently represent a hydrogen atom, an alkyl group which is unsubstituted or has a substituent, an alicyclic group which is unsubstituted or has a substituent, an aryl group which is unsubstituted or has a substituent, a heteroaryl group which is unsubstituted or has a substituent, or a non-aromatic heterocyclic group which is unsubstituted or has a substituent, where a plurality of $R^6$'s may be the same or different from each other, $R^7$'s represent a hydrogen atom or a methyl group, where a plurality of $R^7$'s may be the same or different from each other, Z is a terminal group, and $n_1$ is a natural number of 2 to 10,000).

5. The molded article according to claim 1, wherein the constitutional unit (b) is derived from a monomer selected from the group consisting of methoxymethyl acrylate, methoxyethyl acrylate, methoxypropyl acrylate, methoxybutyl acrylate, ethoxymethyl acrylate, ethoxyethyl acrylate, ethoxypropyl acrylate, ethoxybutyl acrylate, propoxymethyl acrylate, propoxyethyl acrylate, propoxypropyl acrylate, propoxybutyl acrylate, butoxymethyl acrylate, butoxyethyl acrylate, butoxypropyl acrylate, butoxybutyl acrylate, methoxymethyl methacrylate, methoxyethyl methacrylate, methoxypropyl methacrylate, methoxybutyl methacrylate, ethoxymethyl methacrylate, ethoxyethyl methacrylate, ethoxypropyl methacrylate, ethoxybutyl methacrylate, propoxymethyl methacrylate, propoxyethyl methacrylate, propoxypropyl methacrylate, propoxybutyl methacrylate, butoxymethyl methacrylate, butoxyethyl methacrylate, butoxypropyl methacrylate, and butoxybutyl methacrylate.

6. The molded article according to claim 1, wherein the copolymer has a weight-average molecular weight (Mw) of 75,000 or more.

7. The molded article according to claim 1, wherein the molding material further comprises:

a thermoplastic resin, and wherein the molding material contains 1% by mass or more of the copolymer for suppressing protein adsorption.

8. The molded article according to claim 7, wherein the thermoplastic resin is a (meth)acrylic resin or an olefin resin.

9. The molded article according to claim 1, wherein the molded article is any one coming in contact with a plasma protein, which is selected from the group consisting of a medical instrument, a biochemical instrument, and a cell therapy apparatus, or any one coming in contact with a protein other than the plasma protein, which is selected from the group consisting of a petri dish for cell culture, a cell for cell culture, a microplate for cell culture, a bag for cell culture, a plate for cell culture, a tube for cell culture, a flask for cell culture, a petri dish for biopharmacy, a cell for biopharmacy, a microplate for biopharmacy, a plate for biopharmacy, a tube for biopharmacy, a bag for biopharmacy, a container for biopharmacy, a syringe for biopharmacy, a flask for biopharmacy, a petri dish for antibody drug, a cell for antibody drug, a microplate for antibody drug, a plate for antibody drug, a tube for antibody drug, a bag for antibody drug, a container for antibody drug, and a syringe for antibody drug, a flask for antibody drug, a blood bag, a vial for blood product, and a bag for blood product.

10. An article that comes in contact with a protein, comprising:
a coating film on a surface of the article, the surface coming in contact with a protein,
wherein
the coating film is formed with a composition comprising a solvent and a copolymer comprising:
a constitutional unit (a) of Formula (1); and
a constitutional unit (b) of Formula (2),
wherein
a total mass of the constitutional unit (b) is more than a total mass of the constitutional unit (a) in all constitutional units,

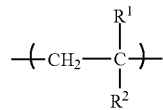

(1)

wherein
$R^1$ represents a hydrogen atom or a methyl group,
$R^2$ is an $OR^{33}$, a halogen atom, $COR^{34}$, $COOR^{35}$, CN, $CONR^{36}R^{37}$, or $R^{38}$, where $R^{33}$ to $R^{37}$ each independently represent a hydrogen atom, a substituted or unsubstituted alkyl group, a substituted or unsubstituted alicyclic group, a substituted or unsubstituted aryl group, a substituted or unsubstituted heteroaryl group, a substituted or unsubstituted non-aromatic heterocyclic group, a substituted or unsubstituted aralkyl group, a substituted or unsubstituted alkaryl group, or a substituted or unsubstituted organosilyl group, and $R^{38}$ represents a substituted or unsubstituted aryl group or a substituted or unsubstituted heteroaryl group,

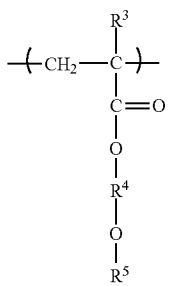

(2)

wherein
$R^3$ represents a hydrogen atom or a methyl group,
$R^4$ represents an alkylene group having 1 to 4 carbon atoms, and
$R^5$ represents a hydrocarbon group having 1 to 6 carbon atoms;
wherein the article having the coating film is any one having the coating film on a surface thereof, where the surface comes in contact with a plasma protein, which is selected from the group consisting of a medical instrument, a biochemical instrument, and a cell therapy apparatus, or any one having the coating film on a surface thereof, where the surface comes in contact with a protein other than the plasma protein, which is selected from the group consisting of a petri dish for cell culture, a cell for cell culture, a microplate for cell culture, a bag for cell culture, a plate for cell culture, a tube for cell culture, a flask for cell culture, a petri dish for biopharmacy, a cell for biopharmacy, a microplate for biopharmacy, a plate for biopharmacy, a tube for biopharmacy, a bag for biopharmacy, a container for biopharmacy, a syringe for biopharmacy, a flask for biopharmacy, a petri dish for antibody drug, a cell for antibody drug, a microplate for antibody drug, a plate for antibody drug, a tube for antibody drug, a bag for antibody drug, a container for antibody drug, and a syringe for antibody drug, a flask for antibody drug, a blood bag, a vial for blood product, and a bag for blood product.

11. The article that comes in contact with a protein according to claim 10, wherein the constitutional unit (a) is a constitutional unit derived from a (meth)acrylic acid ester.

12. The article that comes in contact with a protein according to claim 10, wherein the copolymer further comprises a constitutional unit (d) derived from a macromonomer containing the constitutional unit (a).

13. The article that comes in contact with a protein according to claim 12,
wherein the macromonomer is of Formula (4),

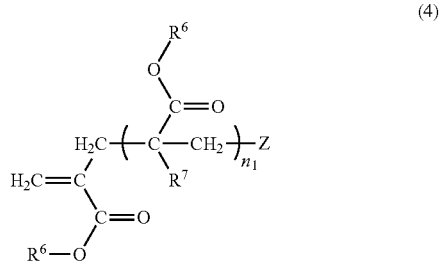

(4)

wherein
$R^6$'s each independently represent a hydrogen atom, an alkyl group which is unsubstituted or has a substituent, an alicyclic group which is unsubstituted or has a substituent, an aryl group which is unsubstituted or has a substituent, a heteroaryl group which is unsubstituted or has a substituent, or a non-aromatic heterocyclic group which is unsubstituted or has a substituent, where a plurality of $R^6$'s may be the same or different from each other,
$R^7$'s represent a hydrogen atom or a methyl group, where a plurality of $R^7$'s may be the same or different from each other,
Z is a terminal group, and
$n_1$ is a natural number of 2 to 10,000).

14. The article that comes in contact with a protein according to claim 10, wherein the constitutional unit (b) is derived from a monomer selected from the group consisting of methoxymethyl acrylate, methoxyethyl acrylate, methoxypropyl acrylate, methoxybutyl acrylate, ethoxymethyl acrylate, ethoxyethyl acrylate, ethoxypropyl acrylate, ethoxybutyl acrylate, propoxymethyl acrylate, propoxyethyl acrylate, propoxypropyl acrylate, propoxybutyl acrylate, butoxymethyl acrylate, butoxyethyl acrylate, butoxypropyl acrylate, butoxybutyl acrylate, methoxymethyl methacrylate, methoxyethyl methacrylate, methoxypropyl methacrylate, methoxybutyl methacrylate, ethoxymethyl methacrylate, ethoxyethyl methacrylate, ethoxypropyl methacrylate, ethoxybutyl methacrylate, propoxymethyl methacrylate, propoxyethyl methacrylate, propoxypropyl methacrylate, propoxybutyl methacrylate, butoxymethyl methacrylate, butoxyethyl methacrylate, butoxypropyl methacrylate, and butoxybutyl methacrylate.

15. The article that comes in contact with a protein according to claim 10, wherein the copolymer has a weight-average molecular weight (Mw) of 75,000 or more.

* * * * *